(12) United States Patent
Ruddenklau et al.

(10) Patent No.: US 9,707,027 B2
(45) Date of Patent: *Jul. 18, 2017

(54) MEDICAL DEVICE

(75) Inventors: David Ian Ruddenklau, Christchuch (NZ); Paul Christopher Roberts, Cambridge (GB); Alan Edward Green, Cambridge (GB)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 469 days.

This patent is subject to a terminal disclaimer.

(21) Appl. No.: 13/810,865

(22) PCT Filed: May 20, 2011

(86) PCT No.: PCT/GB2011/000778
§ 371 (c)(1),
(2), (4) Date: Sep. 11, 2013

(87) PCT Pub. No.: WO2011/144911
PCT Pub. Date: Nov. 24, 2011

(65) Prior Publication Data
US 2013/0345689 A1 Dec. 26, 2013

(30) Foreign Application Priority Data
May 21, 2010 (GB) .................................. 1008510.8

(51) Int. Cl.
*A61B 18/12* (2006.01)
*A61B 17/00* (2006.01)
(Continued)

(52) U.S. Cl.
CPC .......... *A61B 18/12* (2013.01); *A61B 18/1206* (2013.01); *A61B 2017/00734* (2013.01);
(Continued)

(58) Field of Classification Search
CPC . A61B 18/12; A61B 18/1206; A61B 2018/12; A61B 2018/1206; A61B 2018/1226; A61B 2018/1286
(Continued)

(56) References Cited

U.S. PATENT DOCUMENTS 969,528 A    9/1910 Disbrow
1,570,025 A  1/1926 Young
(Continued)

FOREIGN PATENT DOCUMENTS

AU   2003241752 A1   9/2003
CN      1233944 A    11/1999
(Continued)

OTHER PUBLICATIONS

International Search Report for PCT/GB2011/000778, dated Oct. 19, 2011 (8 pages).
(Continued)

*Primary Examiner* — Jaymi Della

(57) ABSTRACT

A medical device is described having a handle and an end effector coupled to the handle. The end effector has at least one electrode for providing electrical signals to a tissue or vessel to be treated. An RF drive circuit is provided for generating an RF drive signal that is applied to the end effector electrode. The RF drive circuit includes a resonant circuit and a frequency controller is used to vary the frequency of a signal passed through the resonant circuit in order to control the power supplied to the end effector electrode.

14 Claims, 10 Drawing Sheets

(51) Int. Cl.
*A61B 18/00* (2006.01)
*A61B 18/14* (2006.01)

(52) U.S. Cl.
CPC ............... *A61B 2018/00595* (2013.01); *A61B 2018/00607* (2013.01); *A61B 2018/00642* (2013.01); *A61B 2018/00732* (2013.01); *A61B 2018/00827* (2013.01); *A61B 2018/00875* (2013.01); *A61B 2018/00892* (2013.01); *A61B 2018/1226* (2013.01); *A61B 2018/1452* (2013.01)

(58) Field of Classification Search
USPC ....................................................... 606/34–38
See application file for complete search history.

(56) References Cited

U.S. PATENT DOCUMENTS

| | | |
|---|---|---|
| 1,813,902 A | 7/1931 | Bovie |
| 2,442,966 A | 6/1948 | Wallace |
| 2,704,333 A | 3/1955 | Calosi et al. |
| 2,736,960 A | 3/1956 | Armstrong |
| 2,849,788 A | 9/1958 | Creek |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,053,124 A | 9/1962 | Balamuth et al. |
| 3,082,805 A | 3/1963 | Royce |
| 3,432,691 A | 3/1969 | Shoh |
| 3,433,226 A | 3/1969 | Boyd |
| 3,489,930 A | 1/1970 | Shoh |
| 3,513,848 A | 5/1970 | Winston et al. |
| 3,526,219 A | 9/1970 | Balamuth |
| 3,554,198 A | 1/1971 | Tatoian et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,776,238 A | 12/1973 | Peyman et al. |
| 3,805,787 A | 4/1974 | Banko |
| 3,809,977 A | 5/1974 | Balamuth et al. |
| 3,830,098 A | 8/1974 | Antonevich |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 4,012,647 A | 3/1977 | Balamuth et al. |
| 4,074,719 A | 2/1978 | Semm |
| 4,156,187 A | 5/1979 | Murry et al. |
| 4,167,944 A | 9/1979 | Banko |
| 4,188,927 A | 2/1980 | Harris |
| 4,200,106 A | 4/1980 | Douvas et al. |
| 4,203,444 A | 5/1980 | Bonnell et al. |
| 4,300,083 A | 11/1981 | Heiges |
| 4,302,728 A | 11/1981 | Nakamura |
| 4,306,570 A | 12/1981 | Matthews |
| 4,445,063 A | 4/1984 | Smith |
| 4,491,132 A | 1/1985 | Aikins |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,545,374 A | 10/1985 | Jacobson |
| 4,574,615 A | 3/1986 | Bower et al. |
| 4,617,927 A | 10/1986 | Manes |
| 4,633,119 A | 12/1986 | Thompson |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,708,127 A | 11/1987 | Abdelghani |
| 4,712,722 A | 12/1987 | Hood et al. |
| 4,819,635 A | 4/1989 | Shapiro |
| 4,827,911 A | 5/1989 | Broadwin et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,850,354 A | 7/1989 | McGurk-Burleson et al. |
| 4,852,578 A | 8/1989 | Companion et al. |
| 4,865,159 A | 9/1989 | Jamison |
| 4,867,157 A | 9/1989 | McGurk-Burleson et al. |
| 4,878,493 A | 11/1989 | Pasternak et al. |
| 4,881,550 A | 11/1989 | Kothe |
| 4,896,009 A | 1/1990 | Pawlowski |
| 4,903,696 A | 2/1990 | Stasz et al. |
| 4,915,643 A | 4/1990 | Samejima et al. |
| 4,922,902 A | 5/1990 | Wuchinich et al. |
| 4,965,532 A | 10/1990 | Sakurai |
| 4,979,952 A | 12/1990 | Kubota et al. |
| 4,981,756 A | 1/1991 | Rhandhawa |
| 5,013,956 A | 5/1991 | Kurozumi et al. |
| 5,015,227 A | 5/1991 | Broadwin et al. |
| 5,026,370 A | 6/1991 | Lottick |
| 5,026,387 A | 6/1991 | Thomas |
| 5,042,707 A | 8/1991 | Taheri |
| 5,084,052 A | 1/1992 | Jacobs |
| 5,105,117 A | 4/1992 | Yamaguchi |
| 5,109,819 A | 5/1992 | Custer et al. |
| 5,112,300 A | 5/1992 | Ureche |
| 5,123,903 A | 6/1992 | Quaid et al. |
| 5,126,618 A | 6/1992 | Takahashi et al. |
| D327,872 S | 7/1992 | McMills et al. |
| 5,152,762 A | 10/1992 | McElhenney |
| 5,162,044 A | 11/1992 | Gahn et al. |
| 5,163,421 A | 11/1992 | Bernstein et al. |
| 5,163,537 A | 11/1992 | Radev |
| 5,167,725 A | 12/1992 | Clark et al. |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,209,719 A | 5/1993 | Baruch et al. |
| 5,213,569 A | 5/1993 | Davis |
| 5,214,339 A | 5/1993 | Naito |
| 5,218,529 A | 6/1993 | Meyer et al. |
| 5,221,282 A | 6/1993 | Wuchinich |
| 5,226,909 A | 7/1993 | Evans et al. |
| 5,226,910 A | 7/1993 | Kajiyama et al. |
| 5,241,236 A | 8/1993 | Sasaki et al. |
| 5,241,968 A | 9/1993 | Slater |
| 5,242,460 A | 9/1993 | Klein et al. |
| 5,254,129 A | 10/1993 | Alexander |
| 5,257,988 A | 11/1993 | L'Esperance, Jr. |
| 5,261,922 A | 11/1993 | Hood |
| 5,263,957 A | 11/1993 | Davison |
| 5,264,925 A | 11/1993 | Shipp et al. |
| 5,275,166 A | 1/1994 | Vaitekunas et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,300,068 A | 4/1994 | Rosar et al. |
| 5,304,115 A | 4/1994 | Pflueger et al. |
| D347,474 S | 5/1994 | Olson |
| 5,312,023 A | 5/1994 | Green et al. |
| 5,312,425 A | 5/1994 | Evans et al. |
| 5,322,055 A | 6/1994 | Davison et al. |

(56) References Cited

U.S. PATENT DOCUMENTS

| | | |
|---|---|---|
| 5,324,299 A | 6/1994 | Davison et al. |
| 5,326,013 A | 7/1994 | Green et al. |
| 5,326,342 A | 7/1994 | Pflueger et al. |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,359,994 A | 11/1994 | Krauter et al. |
| 5,366,466 A | 11/1994 | Christian et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,387,215 A | 2/1995 | Fisher |
| 5,389,098 A | 2/1995 | Tsuruta et al. |
| 5,394,187 A | 2/1995 | Shipp |
| 5,396,266 A | 3/1995 | Brimhall |
| 5,403,312 A | 4/1995 | Yates et al. |
| 5,403,334 A | 4/1995 | Evans et al. |
| 5,408,268 A | 4/1995 | Shipp |
| D358,887 S | 5/1995 | Feinberg |
| 5,411,481 A | 5/1995 | Allen et al. |
| 5,419,761 A | 5/1995 | Narayanan et al. |
| 5,421,829 A | 6/1995 | Olichney et al. |
| 5,423,844 A | 6/1995 | Miller |
| 5,438,997 A | 8/1995 | Sieben et al. |
| 5,445,639 A | 8/1995 | Kuslich et al. |
| 5,449,370 A | 9/1995 | Vaitekunas |
| 5,451,220 A | 9/1995 | Ciervo |
| 5,456,684 A | 10/1995 | Schmidt et al. |
| 5,471,988 A | 12/1995 | Fujio et al. |
| 5,472,443 A | 12/1995 | Cordis et al. |
| 5,478,003 A | 12/1995 | Green et al. |
| 5,483,501 A | 1/1996 | Park et al. |
| 5,486,162 A | 1/1996 | Brumbach |
| 5,490,860 A | 2/1996 | Middle et al. |
| 5,500,216 A | 3/1996 | Julian et al. |
| 5,501,654 A | 3/1996 | Failla et al. |
| 5,505,693 A | 4/1996 | Mackool |
| 5,507,738 A | 4/1996 | Ciervo |
| 5,527,331 A | 6/1996 | Kresch et al. |
| 5,540,693 A | 7/1996 | Fisher |
| 5,558,671 A | 9/1996 | Yates |
| 5,562,609 A | 10/1996 | Brumbach |
| 5,562,610 A | 10/1996 | Brumbach |
| 5,573,424 A | 11/1996 | Poppe |
| 5,577,654 A | 11/1996 | Bishop |
| 5,591,187 A | 1/1997 | Dekel |
| 5,593,414 A | 1/1997 | Shipp et al. |
| 5,601,601 A | 2/1997 | Tal et al. |
| 5,603,773 A | 2/1997 | Campbell |
| 5,607,436 A | 3/1997 | Pratt et al. |
| 5,618,304 A | 4/1997 | Hart et al. |
| 5,618,492 A | 4/1997 | Auten et al. |
| 5,620,447 A | 4/1997 | Smith et al. |
| 5,626,595 A | 5/1997 | Sklar et al. |
| 5,628,760 A | 5/1997 | Knoepfler |
| 5,630,420 A | 5/1997 | Vaitekunas |
| D381,077 S | 7/1997 | Hunt |
| 5,651,780 A | 7/1997 | Jackson et al. |
| 5,653,713 A | 8/1997 | Michelson |
| 5,669,922 A | 9/1997 | Hood |
| 5,674,235 A | 10/1997 | Parisi |
| 5,678,568 A | 10/1997 | Uchikubo et al. |
| 5,690,269 A | 11/1997 | Bolanos et al. |
| 5,694,936 A | 12/1997 | Fujimoto et al. |
| 5,704,534 A | 1/1998 | Huitema et al. |
| 5,709,680 A | 1/1998 | Yates et al. |
| 5,711,472 A | 1/1998 | Bryan |
| 5,713,896 A | 2/1998 | Nardella |
| 5,717,306 A | 2/1998 | Shipp |
| 5,728,130 A | 3/1998 | Ishikawa et al. |
| 5,730,752 A | 3/1998 | Alden et al. |
| 5,733,074 A | 3/1998 | Stöck et al. |
| 5,741,226 A | 4/1998 | Strukel et al. |
| 5,766,164 A | 6/1998 | Mueller et al. |
| 5,772,659 A | 6/1998 | Becker et al. |
| 5,792,135 A | 8/1998 | Madhani et al. |
| 5,792,138 A | 8/1998 | Shipp |
| 5,792,165 A | 8/1998 | Klieman et al. |
| 5,805,140 A | 9/1998 | Rosenberg et al. |
| 5,808,396 A | 9/1998 | Boukhny |
| 5,810,859 A | 9/1998 | DiMatteo et al. |
| 5,817,084 A | 10/1998 | Jensen |
| 5,817,119 A | 10/1998 | Klieman et al. |
| 5,823,197 A | 10/1998 | Edwards |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,957 A | 11/1998 | Schulz et al. |
| 5,843,109 A | 12/1998 | Mehta et al. |
| 5,851,212 A | 12/1998 | Zirps et al. |
| 5,858,018 A | 1/1999 | Shipp et al. |
| 5,873,873 A | 2/1999 | Smith et al. |
| 5,873,882 A | 2/1999 | Straub et al. |
| 5,878,193 A | 3/1999 | Wang et al. |
| 5,879,364 A | 3/1999 | Bromfield et al. |
| 5,883,615 A | 3/1999 | Fago et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,627 A | 5/1999 | Spaulding |
| 5,906,628 A | 5/1999 | Miyawaki et al. |
| 5,911,699 A | 6/1999 | Anis et al. |
| 5,916,229 A | 6/1999 | Evans |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,024,741 A | 2/2000 | Williamson, IV et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,048,224 A | 4/2000 | Kay |
| 6,050,943 A | 4/2000 | Slayton et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,647 A | 5/2000 | Witt et al. |
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |

(56) References Cited

U.S. PATENT DOCUMENTS

| | | |
|---|---|---|
| 6,096,033 A | 8/2000 | Tu et al. |
| 6,099,542 A | 8/2000 | Cohn et al. |
| 6,109,500 A | 8/2000 | Alli et al. |
| 6,110,127 A | 8/2000 | Suzuki |
| 6,113,594 A | 9/2000 | Savage |
| 6,117,152 A | 9/2000 | Huitema |
| 6,126,629 A | 10/2000 | Perkins |
| 6,129,735 A | 10/2000 | Okada et al. |
| 6,129,740 A | 10/2000 | Michelson |
| 6,132,368 A | 10/2000 | Cooper |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,147,560 A | 11/2000 | Erhage et al. |
| 6,152,902 A | 11/2000 | Christian et al. |
| 6,154,198 A | 11/2000 | Rosenberg |
| 6,159,160 A | 12/2000 | Hsei et al. |
| 6,159,175 A | 12/2000 | Strukel et al. |
| 6,162,194 A | 12/2000 | Shipp |
| 6,165,150 A | 12/2000 | Banko |
| 6,174,310 B1 | 1/2001 | Kirwan, Jr. |
| 6,179,853 B1 | 1/2001 | Sachse et al. |
| 6,183,426 B1 | 2/2001 | Akisada et al. |
| 6,193,709 B1 | 2/2001 | Miyawaki et al. |
| 6,204,592 B1 | 3/2001 | Hur |
| 6,205,855 B1 | 3/2001 | Pfeiffer |
| 6,206,844 B1 | 3/2001 | Reichel et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,231,565 B1 | 5/2001 | Tovey et al. |
| 6,233,476 B1 | 5/2001 | Strommer et al. |
| 6,238,366 B1 | 5/2001 | Savage et al. |
| 6,245,065 B1 | 6/2001 | Panescu et al. |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,306,157 B1 | 10/2001 | Shchervinsky |
| 6,309,400 B2 | 10/2001 | Beaupre |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,338,657 B1 | 1/2002 | Harper et al. |
| 6,340,352 B1 | 1/2002 | Okada et al. |
| 6,350,269 B1 | 2/2002 | Shipp et al. |
| 6,352,532 B1 | 3/2002 | Kramer et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,109 B1 | 5/2002 | Davison et al. |
| 6,388,657 B1 | 5/2002 | Natoli |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,733 B1 | 6/2002 | Fogarty et al. |
| 6,416,486 B1 | 7/2002 | Wampler |
| 6,423,073 B2 | 7/2002 | Bowman |
| 6,423,082 B1 | 7/2002 | Houser et al. |
| 6,428,539 B1 | 8/2002 | Baxter et al. |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,142 B1 | 10/2002 | Faller et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,708 B2 | 12/2002 | Madan et al. |
| 6,497,715 B2 | 12/2002 | Satou |
| 6,500,176 B1 | 12/2002 | Truckai et al. |
| 6,500,188 B2 | 12/2002 | Harper et al. |
| 6,500,312 B2 | 12/2002 | Wedekamp |
| 6,506,208 B2 | 1/2003 | Hunt et al. |
| 6,511,478 B1 | 1/2003 | Burnside et al. |
| 6,511,493 B1 | 1/2003 | Moutafis et al. |
| 6,514,267 B2 | 2/2003 | Jewett |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,558,376 B2 | 5/2003 | Bishop |
| 6,561,983 B2 | 5/2003 | Cronin et al. |
| 6,565,558 B1 * | 5/2003 | Lindenmeier et al. .......... 606/34 |
| 6,572,563 B2 | 6/2003 | Ouchi |
| 6,572,632 B2 | 6/2003 | Zisterer et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| D477,408 S | 7/2003 | Bromley |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,607,540 B1 | 8/2003 | Shipp |
| 6,610,059 B1 | 8/2003 | West, Jr. |
| 6,616,450 B2 | 9/2003 | Mossle et al. |
| 6,619,529 B2 | 9/2003 | Green et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,633,234 B2 | 10/2003 | Wiener et al. |
| 6,644,532 B2 | 11/2003 | Green et al. |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,710 B2 | 12/2003 | Moutafis et al. |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,899 B2 | 1/2004 | Wiener et al. |
| 6,682,544 B2 | 1/2004 | Mastri et al. |

(56) References Cited

U.S. PATENT DOCUMENTS

| | | |
|---|---|---|
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,716,215 B1 | 4/2004 | David et al. |
| 6,719,692 B2 | 4/2004 | Kleffner et al. |
| 6,719,776 B2 | 4/2004 | Baxter |
| 6,723,091 B2 | 4/2004 | Goble et al. |
| D490,059 S | 5/2004 | Conway et al. |
| 6,731,047 B2 | 5/2004 | Kauf et al. |
| 6,733,506 B1 | 5/2004 | McDevitt et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,770,072 B1 | 8/2004 | Truckai et al. |
| 6,773,409 B2 | 8/2004 | Truckai et al. |
| 6,773,443 B2 | 8/2004 | Truwit et al. |
| 6,773,444 B2 | 8/2004 | Messerly |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,790,173 B2 | 9/2004 | Saadat et al. |
| 6,790,216 B1 | 9/2004 | Ishikawa |
| 6,796,981 B2 | 9/2004 | Wham et al. |
| D496,997 S | 10/2004 | Dycus et al. |
| 6,802,843 B2 | 10/2004 | Truckai et al. |
| 6,809,508 B2 | 10/2004 | Donofrio |
| 6,810,281 B2 | 10/2004 | Brock et al. |
| 6,827,712 B2 | 12/2004 | Tovey et al. |
| 6,828,712 B2 | 12/2004 | Battaglin et al. |
| 6,835,082 B2 | 12/2004 | Gonnering |
| 6,849,073 B2 | 2/2005 | Hoey et al. |
| 6,860,878 B2 | 3/2005 | Brock |
| 6,863,676 B2 | 3/2005 | Lee et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,899,685 B2 | 5/2005 | Kermode et al. |
| 6,905,497 B2 | 6/2005 | Truckai et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,926,712 B2 | 8/2005 | Phan |
| 6,926,716 B2 | 8/2005 | Baker et al. |
| 6,929,602 B2 | 8/2005 | Hirakui et al. |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,994,708 B2 | 2/2006 | Manzo |
| 7,001,335 B2 | 2/2006 | Adachi et al. |
| 7,011,657 B2 | 3/2006 | Truckai et al. |
| 7,014,638 B2 | 3/2006 | Michelson |
| 7,033,357 B2 | 4/2006 | Baxter et al. |
| 7,037,306 B2 | 5/2006 | Podany |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,066,893 B2 | 6/2006 | Hibner et al. |
| 7,066,895 B2 | 6/2006 | Podany |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,619 B2 | 8/2006 | Truckai et al. |
| 7,087,054 B2 | 8/2006 | Truckai et al. |
| 7,090,672 B2 | 8/2006 | Underwood et al. |
| 7,101,371 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| D531,311 S | 10/2006 | Guerra et al. |
| 7,117,034 B2 | 10/2006 | Kronberg |
| 7,118,564 B2 | 10/2006 | Ritchie et al. |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,144,403 B2 | 12/2006 | Booth |
| 7,153,315 B2 | 12/2006 | Miller |
| D536,093 S | 1/2007 | Nakajima et al. |
| 7,156,189 B1 | 1/2007 | Bar-Cohen et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,296 B2 | 1/2007 | Pearson et al. |
| 7,160,299 B2 | 1/2007 | Baily |
| 7,163,548 B2 | 1/2007 | Stulen et al. |
| 7,169,144 B2 | 1/2007 | Hoey et al. |
| 7,169,146 B2 | 1/2007 | Truckai et al. |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| D541,418 S | 4/2007 | Schechter et al. |
| 7,204,820 B2 | 4/2007 | Akahoshi |
| 7,207,997 B2 | 4/2007 | Shipp et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,229,455 B2 | 6/2007 | Sakurai et al. |
| 7,235,071 B2 | 6/2007 | Gonnering |
| 7,244,262 B2 | 7/2007 | Wiener et al. |
| 7,258,688 B1 | 8/2007 | Shah et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupré |
| 7,300,431 B2 | 11/2007 | Dubrovsky |
| 7,300,435 B2 | 11/2007 | Wham et al. |
| 7,300,446 B2 | 11/2007 | Beaupre |
| 7,303,531 B2 | 12/2007 | Lee et al. |
| 7,303,557 B2 | 12/2007 | Wham et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |

(56) References Cited

U.S. PATENT DOCUMENTS

| | | |
|---|---|---|
| 7,318,831 B2 | 1/2008 | Alvarez et al. |
| 7,326,236 B2 | 2/2008 | Andreas et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckal et al. |
| 7,364,577 B2 | 4/2008 | Wham et al. |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,390,317 B2 | 6/2008 | Taylor et al. |
| 7,404,508 B2 | 7/2008 | Smith et al. |
| 7,408,288 B2 | 8/2008 | Hara |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,441,684 B2 | 10/2008 | Shelton, IV et al. |
| 7,455,208 B2 | 11/2008 | Wales et al. |
| 7,462,181 B2 | 12/2008 | Kraft et al. |
| 7,464,846 B2 | 12/2008 | Shelton, IV et al. |
| 7,472,815 B2 | 1/2009 | Shelton, IV et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,494,468 B2 | 2/2009 | Rabiner et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,524,320 B2 | 4/2009 | Tierney et al. |
| 7,530,986 B2 | 5/2009 | Beaupre et al. |
| 7,534,243 B1 | 5/2009 | Chin et al. |
| D594,983 S | 6/2009 | Price et al. |
| 7,540,871 B2 | 6/2009 | Gonnering |
| 7,544,200 B2 | 6/2009 | Houser |
| 7,549,564 B2 | 6/2009 | Boudreaux |
| 7,559,450 B2 | 7/2009 | Wales et al. |
| 7,567,012 B2 | 7/2009 | Namikawa |
| 7,569,057 B2 | 8/2009 | Liu et al. |
| 7,572,266 B2 | 8/2009 | Young et al. |
| 7,578,820 B2 | 8/2009 | Moore et al. |
| 7,582,084 B2 | 9/2009 | Swanson et al. |
| 7,582,095 B2 | 9/2009 | Shipp et al. |
| 7,585,181 B2 | 9/2009 | Olsen |
| 7,588,176 B2 | 9/2009 | Timm et al. |
| 7,601,119 B2 | 10/2009 | Shahinian |
| 7,621,930 B2 | 11/2009 | Houser |
| 7,641,653 B2 | 1/2010 | Dalla Betta et al. |
| 7,654,431 B2 | 2/2010 | Hueil et al. |
| 7,659,833 B2 | 2/2010 | Warner et al. |
| 7,665,647 B2 | 2/2010 | Shelton, IV et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,098 B2 | 4/2010 | Wallace et al. |
| 7,699,846 B2 | 4/2010 | Ryan |
| 7,713,202 B2 | 5/2010 | Boukhny et al. |
| 7,714,481 B2 | 5/2010 | Sakai |
| 7,717,915 B2 | 5/2010 | Miyazawa |
| D618,797 S | 6/2010 | Price et al. |
| 7,726,537 B2 | 6/2010 | Olson et al. |
| 7,738,969 B2 | 6/2010 | Bleich |
| 7,740,594 B2 | 6/2010 | Hibner |
| 7,751,115 B2 | 7/2010 | Song |
| D621,503 S | 8/2010 | Otten et al. |
| 7,766,210 B2 | 8/2010 | Shelton, IV et al. |
| 7,766,693 B2 | 8/2010 | Sartor et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,784,662 B2 | 8/2010 | Wales et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,045 B2 | 9/2010 | Masuda |
| 7,803,152 B2 | 9/2010 | Honda et al. |
| 7,806,891 B2 | 10/2010 | Nowlin et al. |
| 7,810,693 B2 | 10/2010 | Broehl et al. |
| 7,819,819 B2 | 10/2010 | Quick et al. |
| D627,066 S | 11/2010 | Romero |
| 7,824,401 B2 | 11/2010 | Manzo et al. |
| 7,832,611 B2 | 11/2010 | Boyden et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,876,030 B2 | 1/2011 | Taki et al. |
| D631,965 S | 2/2011 | Price et al. |
| 7,878,991 B2 | 2/2011 | Babaev |
| 7,879,033 B2 | 2/2011 | Sartor et al. |
| 7,892,606 B2 | 2/2011 | Thies et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,824 B2 | 3/2011 | Masuda et al. |
| 7,922,061 B2 | 4/2011 | Shelton, IV et al. |
| 7,922,651 B2 | 4/2011 | Yamada et al. |
| D637,288 S | 5/2011 | Houghton |
| D638,540 S | 5/2011 | Ijiri et al. |
| 7,936,203 B2 | 5/2011 | Zimlich |
| 7,951,095 B2 | 5/2011 | Makin et al. |
| 7,951,165 B2 | 5/2011 | Golden et al. |
| 7,959,050 B2 | 6/2011 | Smith et al. |
| 7,959,626 B2 | 6/2011 | Hong et al. |
| 7,972,329 B2 | 7/2011 | Refior et al. |
| 7,976,544 B2 | 7/2011 | McClurken et al. |
| 7,981,050 B2 | 7/2011 | Ritchart et al. |
| 7,998,157 B2 | 8/2011 | Culp et al. |
| 8,038,693 B2 | 10/2011 | Allen |
| 8,057,498 B2 | 11/2011 | Robertson |
| 8,058,771 B2 | 11/2011 | Giordano et al. |
| 8,061,014 B2 | 11/2011 | Smith et al. |
| 8,070,711 B2 | 12/2011 | Bassinger et al. |
| 8,070,762 B2 | 12/2011 | Escudero et al. |
| 8,075,558 B2 | 12/2011 | Truckai et al. |
| 8,089,197 B2 | 1/2012 | Rinner et al. |
| 8,097,012 B2 | 1/2012 | Kagarise |
| 8,105,323 B2 | 1/2012 | Buysse et al. |
| 8,142,461 B2 | 3/2012 | Houser et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,172,846 B2 | 5/2012 | Brunnett et al. |

(56) References Cited

U.S. PATENT DOCUMENTS

| | | |
|---|---|---|
| 8,172,870 B2 | 5/2012 | Shipp |
| 8,177,800 B2 | 5/2012 | Spitz et al. |
| 8,182,502 B2 | 5/2012 | Stulen et al. |
| 8,186,877 B2 | 5/2012 | Klimovitch et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,502 B2 | 6/2012 | Smith et al. |
| 8,210,411 B2 | 7/2012 | Yates et al. |
| 8,226,675 B2 | 7/2012 | Houser et al. |
| 8,235,917 B2 | 8/2012 | Joseph et al. |
| 8,236,019 B2 | 8/2012 | Houser |
| 8,236,020 B2 | 8/2012 | Smith et al. |
| 8,246,575 B2 | 8/2012 | Viola |
| 8,246,615 B2 | 8/2012 | Behnke |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,273,087 B2 | 9/2012 | Kimura et al. |
| D669,992 S | 10/2012 | Schafer et al. |
| D669,993 S | 10/2012 | Merchant et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,298,223 B2 | 10/2012 | Wham et al. |
| 8,298,225 B2 | 10/2012 | Gilbert |
| 8,303,576 B2 | 11/2012 | Brock |
| 8,303,580 B2 | 11/2012 | Wham et al. |
| 8,303,583 B2 | 11/2012 | Hosier et al. |
| 8,319,400 B2 | 11/2012 | Houser et al. |
| 8,323,302 B2 | 12/2012 | Robertson et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,344,596 B2 | 1/2013 | Nield et al. |
| 8,348,967 B2 | 1/2013 | Stulen |
| 8,357,103 B2 | 1/2013 | Mark et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,059 B2 | 2/2013 | Deville et al. |
| 8,377,085 B2 | 2/2013 | Smith et al. |
| 8,382,782 B2 | 2/2013 | Robertson et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,425,545 B2 | 4/2013 | Smith et al. |
| 8,430,898 B2 | 4/2013 | Wiener et al. |
| 8,435,257 B2 | 5/2013 | Smith et al. |
| 8,439,912 B2 | 5/2013 | Cunningham et al. |
| 8,439,939 B2 | 5/2013 | Deville et al. |
| 8,444,637 B2 | 5/2013 | Podmore et al. |
| 8,444,662 B2 | 5/2013 | Palmer et al. |
| 8,444,664 B2 | 5/2013 | Balanev et al. |
| 8,461,744 B2 | 6/2013 | Wiener et al. |
| 8,469,981 B2 | 6/2013 | Robertson et al. |
| 8,479,969 B2 | 7/2013 | Shelton, IV |
| 8,480,703 B2 | 7/2013 | Nicholas et al. |
| 8,485,413 B2 | 7/2013 | Scheib et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| D687,549 S | 8/2013 | Johnson et al. |
| 8,509,318 B2 | 8/2013 | Tailliet |
| 8,512,359 B2 | 8/2013 | Whitman et al. |
| 8,512,365 B2 | 8/2013 | Wiener et al. |
| 8,523,889 B2 | 9/2013 | Stulen et al. |
| 8,531,064 B2 | 9/2013 | Robertson et al. |
| 8,535,340 B2 | 9/2013 | Allen |
| 8,535,341 B2 | 9/2013 | Allen |
| 8,546,996 B2 | 10/2013 | Messerly et al. |
| 8,546,999 B2 | 10/2013 | Houser et al. |
| 8,568,400 B2 | 10/2013 | Gilbert |
| 8,573,461 B2 | 11/2013 | Shelton, IV et al. |
| 8,573,465 B2 | 11/2013 | Shelton, IV |
| 8,579,928 B2 | 11/2013 | Robertson et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,602,031 B2 | 12/2013 | Reis et al. |
| 8,602,288 B2 | 12/2013 | Shelton, IV et al. |
| 8,608,745 B2 | 12/2013 | Guzman et al. |
| 8,616,431 B2 | 12/2013 | Timm et al. |
| 8,623,027 B2 | 1/2014 | Price et al. |
| 8,650,728 B2 | 2/2014 | Wan et al. |
| 8,652,155 B2 | 2/2014 | Houser et al. |
| 8,659,208 B1 | 2/2014 | Rose et al. |
| 8,663,220 B2 | 3/2014 | Wiener et al. |
| 8,690,582 B2 | 4/2014 | Rohrbach et al. |
| 8,696,366 B2 | 4/2014 | Chen et al. |
| 8,704,425 B2 | 4/2014 | Giordano et al. |
| 8,709,031 B2 | 4/2014 | Stulen |
| 8,749,116 B2 | 6/2014 | Messerly et al. |
| 8,752,749 B2 | 6/2014 | Moore et al. |
| 8,754,570 B2 | 6/2014 | Voegele et al. |
| 8,764,735 B2 | 7/2014 | Coe et al. |
| 8,773,001 B2 | 7/2014 | Wiener et al. |
| 8,779,648 B2 | 7/2014 | Giordano et al. |
| 8,808,319 B2 | 8/2014 | Houser et al. |
| 8,827,992 B2 | 9/2014 | Koss et al. |
| 8,845,537 B2 | 9/2014 | Tanaka et al. |
| 8,882,791 B2 | 11/2014 | Stulen |
| 8,888,776 B2 | 11/2014 | Dietz et al. |
| 8,888,809 B2 | 11/2014 | Davison et al. |
| 8,900,259 B2 | 12/2014 | Houser et al. |
| 8,911,460 B2 | 12/2014 | Neurohr et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,961,547 B2 | 2/2015 | Dietz et al. |
| 8,974,477 B2 | 3/2015 | Yamada |
| 8,979,890 B2 | 3/2015 | Boudreaux |
| 8,986,302 B2 | 3/2015 | Aldridge et al. |
| 9,039,695 B2 | 5/2015 | Giordano et al. |
| 9,044,261 B2 | 6/2015 | Houser |
| 2001/0025173 A1 | 9/2001 | Ritchie et al. |
| 2001/0025183 A1 | 9/2001 | Shahidi et al. |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0029055 A1 | 3/2002 | Bonutti |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0156466 A1 | 10/2002 | Sakurai et al. |
| 2002/0156493 A1 | 10/2002 | Houser et al. |
| 2003/0014087 A1 | 1/2003 | Fang et al. |
| 2003/0036705 A1 | 2/2003 | Hare et al. |
| 2003/0050572 A1 | 3/2003 | Brautigam et al. |
| 2003/0055443 A1 | 3/2003 | Spotnitz |
| 2003/0114851 A1 | 6/2003 | Truckai et al. |
| 2003/0144680 A1 | 7/2003 | Kellogg et al. |
| 2003/0199794 A1 | 10/2003 | Sakurai et al. |
| 2003/0204199 A1 | 10/2003 | Novak et al. |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0229344 A1 | 12/2003 | Dycus et al. |

(56) References Cited

U.S. PATENT DOCUMENTS

| | | |
|---|---|---|
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0092921 A1 | 5/2004 | Kadziauskas et al. |
| 2004/0092992 A1 | 5/2004 | Adams et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0132383 A1 | 7/2004 | Langford et al. |
| 2004/0147934 A1 | 7/2004 | Kiester |
| 2004/0167508 A1 | 8/2004 | Wham et al. |
| 2004/0176686 A1 | 9/2004 | Hare et al. |
| 2004/0199193 A1 | 10/2004 | Hayashi et al. |
| 2004/0204728 A1 | 10/2004 | Haefner |
| 2004/0243147 A1 | 12/2004 | Lipow |
| 2004/0260300 A1 | 12/2004 | Gorensek et al. |
| 2005/0021018 A1 | 1/2005 | Anderson et al. |
| 2005/0021065 A1 | 1/2005 | Yamada et al. |
| 2005/0033337 A1 | 2/2005 | Muir et al. |
| 2005/0049546 A1 | 3/2005 | Messerly et al. |
| 2005/0070800 A1 | 3/2005 | Takahashi |
| 2005/0096683 A1 | 5/2005 | Ellins et al. |
| 2005/0099824 A1 | 5/2005 | Dowling et al. |
| 2005/0103819 A1 | 5/2005 | Racenet et al. |
| 2005/0143769 A1 | 6/2005 | White et al. |
| 2005/0149108 A1 | 7/2005 | Cox |
| 2005/0165345 A1 | 7/2005 | Laufer et al. |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0209620 A1 | 9/2005 | Du et al. |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261581 A1 | 11/2005 | Hughes et al. |
| 2005/0261588 A1 | 11/2005 | Makin et al. |
| 2005/0273090 A1 | 12/2005 | Nieman et al. |
| 2005/0288659 A1 | 12/2005 | Kimura et al. |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0066181 A1 | 3/2006 | Bromfield et al. |
| 2006/0074442 A1 | 4/2006 | Noriega et al. |
| 2006/0079879 A1 | 4/2006 | Faller et al. |
| 2006/0084963 A1 | 4/2006 | Messerly |
| 2006/0095046 A1 | 5/2006 | Trieu et al. |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0235306 A1 | 10/2006 | Cotter et al. |
| 2006/0247558 A1 | 11/2006 | Yamada |
| 2006/0253050 A1 | 11/2006 | Yoshimine et al. |
| 2006/0264809 A1 | 11/2006 | Hansmann et al. |
| 2007/0016235 A1 | 1/2007 | Tanaka et al. |
| 2007/0016236 A1 | 1/2007 | Beaupre |
| 2007/0055228 A1 | 3/2007 | Berg et al. |
| 2007/0056596 A1 | 3/2007 | Fanney et al. |
| 2007/0060915 A1 | 3/2007 | Kucklick |
| 2007/0060935 A1 | 3/2007 | Schwardt et al. |
| 2007/0063618 A1 | 3/2007 | Bromfield |
| 2007/0074584 A1 | 4/2007 | Talarico et al. |
| 2007/0106317 A1 | 5/2007 | Shelton, IV et al. |
| 2007/0129716 A1 | 6/2007 | Daw et al. |
| 2007/0130771 A1 | 6/2007 | Ehlert et al. |
| 2007/0131034 A1 | 6/2007 | Ehlert et al. |
| 2007/0149881 A1 | 6/2007 | Rabin |
| 2007/0162050 A1 | 7/2007 | Sartor |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0175949 A1 | 8/2007 | Shelton, IV et al. |
| 2007/0185380 A1 | 8/2007 | Kucklick |
| 2007/0191712 A1 | 8/2007 | Messerly et al. |
| 2007/0219481 A1 | 9/2007 | Babaev |
| 2007/0239028 A1 | 10/2007 | Houser et al. |
| 2007/0239101 A1 | 10/2007 | Kellogg |
| 2007/0249941 A1 | 10/2007 | Salehi et al. |
| 2007/0260234 A1 | 11/2007 | McCullagh et al. |
| 2007/0265560 A1 | 11/2007 | Soltani et al. |
| 2007/0275348 A1 | 11/2007 | Lemon |
| 2007/0282335 A1 | 12/2007 | Young et al. |
| 2007/0287933 A1 | 12/2007 | Phan et al. |
| 2007/0288055 A1* | 12/2007 | Lee ............................. 606/209 |
| 2008/0009848 A1 | 1/2008 | Paraschiv et al. |
| 2008/0051812 A1 | 2/2008 | Schmitz et al. |
| 2008/0058585 A1 | 3/2008 | Novak et al. |
| 2008/0058775 A1 | 3/2008 | Darian et al. |
| 2008/0058845 A1 | 3/2008 | Shimizu et al. |
| 2008/0082039 A1 | 4/2008 | Babaev |
| 2008/0082098 A1 | 4/2008 | Tanaka et al. |
| 2008/0114364 A1 | 5/2008 | Goldin et al. |
| 2008/0125768 A1 | 5/2008 | Tahara et al. |
| 2008/0140158 A1 | 6/2008 | Hamel et al. |
| 2008/0147092 A1 | 6/2008 | Rogge et al. |
| 2008/0171938 A1 | 7/2008 | Masuda et al. |
| 2008/0172051 A1 | 7/2008 | Masuda et al. |
| 2008/0177268 A1 | 7/2008 | Daum et al. |
| 2008/0188878 A1 | 8/2008 | Young |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243106 A1 | 10/2008 | Coe et al. |
| 2008/0243162 A1 | 10/2008 | Shibata et al. |
| 2008/0245371 A1 | 10/2008 | Gruber |
| 2008/0249553 A1 | 10/2008 | Gruber et al. |
| 2008/0255423 A1 | 10/2008 | Kondo et al. |
| 2008/0262490 A1 | 10/2008 | Williams |
| 2008/0281200 A1 | 11/2008 | Voic et al. |
| 2008/0281315 A1 | 11/2008 | Gines |
| 2008/0281322 A1 | 11/2008 | Sherman et al. |
| 2008/0287948 A1 | 11/2008 | Newton et al. |
| 2009/0023985 A1 | 1/2009 | Ewers |
| 2009/0048537 A1 | 2/2009 | Lydon et al. |
| 2009/0054886 A1 | 2/2009 | Yachi et al. |
| 2009/0054894 A1 | 2/2009 | Yachi |
| 2009/0076506 A1 | 3/2009 | Baker |
| 2009/0082716 A1 | 3/2009 | Akahoshi |
| 2009/0112229 A1 | 4/2009 | Omori et al. |
| 2009/0118751 A1 | 5/2009 | Wiener et al. |
| 2009/0118802 A1 | 5/2009 | Mioduski et al. |
| 2009/0138006 A1 | 5/2009 | Bales et al. |
| 2009/0143799 A1 | 6/2009 | Smith et al. |
| 2009/0143800 A1 | 6/2009 | Deville et al. |
| 2009/0143806 A1 | 6/2009 | Witt et al. |
| 2009/0149801 A1 | 6/2009 | Crandall et al. |
| 2009/0207923 A1 | 8/2009 | Dress |
| 2009/0216157 A1 | 8/2009 | Yamada |
| 2009/0223033 A1 | 9/2009 | Houser |
| 2009/0254077 A1 | 10/2009 | Craig |
| 2009/0254080 A1 | 10/2009 | Honda |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270899 A1 | 10/2009 | Carusillo et al. |
| 2009/0275940 A1 | 11/2009 | Malackowski et al. |
| 2009/0318945 A1 | 12/2009 | Yoshimine et al. |
| 2009/0327715 A1 | 12/2009 | Smith et al. |
| 2010/0004508 A1 | 1/2010 | Naito et al. |
| 2010/0016785 A1 | 1/2010 | Takuma |
| 2010/0016852 A1 | 1/2010 | Manzo et al. |
| 2010/0022825 A1 | 1/2010 | Yoshie |
| 2010/0030233 A1 | 2/2010 | Whitman et al. |
| 2010/0030248 A1 | 2/2010 | Palmer et al. |
| 2010/0036370 A1 | 2/2010 | Mirel et al. |

(56) References Cited

U.S. PATENT DOCUMENTS

| | | |
|---|---|---|
| 2010/0042077 A1 | 2/2010 | Okada |
| 2010/0049180 A1 | 2/2010 | Wells et al. |
| 2010/0063525 A1 | 3/2010 | Beaupre et al. |
| 2010/0063528 A1 | 3/2010 | Beaupré |
| 2010/0069940 A1 | 3/2010 | Miller et al. |
| 2010/0158307 A1 | 6/2010 | Kubota et al. |
| 2010/0187283 A1 | 7/2010 | Crainich et al. |
| 2010/0222714 A1 | 9/2010 | Muir et al. |
| 2010/0228264 A1 | 9/2010 | Robinson et al. |
| 2010/0234906 A1 | 9/2010 | Koh |
| 2010/0262134 A1 | 10/2010 | Jensen et al. |
| 2010/0274160 A1 | 10/2010 | Yachi et al. |
| 2010/0280407 A1 | 11/2010 | Polster |
| 2010/0292691 A1 | 11/2010 | Brogna |
| 2010/0298743 A1 | 11/2010 | Nield et al. |
| 2010/0298851 A1 | 11/2010 | Nield |
| 2010/0331742 A1 | 12/2010 | Masuda |
| 2011/0004233 A1 | 1/2011 | Muir et al. |
| 2011/0009850 A1 | 1/2011 | Main et al. |
| 2011/0077648 A1 | 3/2011 | Lee et al. |
| 2011/0082486 A1 | 4/2011 | Messerly et al. |
| 2011/0087215 A1 | 4/2011 | Aldridge et al. |
| 2011/0087217 A1 | 4/2011 | Yates et al. |
| 2011/0087218 A1 | 4/2011 | Boudreaux et al. |
| 2011/0087256 A1 | 4/2011 | Wiener et al. |
| 2011/0112526 A1 | 5/2011 | Fritz et al. |
| 2011/0125151 A1* | 5/2011 | Strauss et al. .................. 606/37 |
| 2011/0125174 A1 | 5/2011 | Babaev |
| 2011/0144806 A1 | 6/2011 | Sandhu et al. |
| 2011/0196399 A1 | 8/2011 | Robertson et al. |
| 2011/0224689 A1 | 9/2011 | Larkin et al. |
| 2011/0238065 A1 | 9/2011 | Hunt et al. |
| 2011/0257650 A1 | 10/2011 | Deville et al. |
| 2011/0270126 A1 | 11/2011 | Gunday et al. |
| 2011/0290853 A1 | 12/2011 | Shelton, IV et al. |
| 2011/0290856 A1 | 12/2011 | Shelton, IV et al. |
| 2012/0004655 A1 | 1/2012 | Kim et al. |
| 2012/0022525 A1 | 1/2012 | Dietz et al. |
| 2012/0022530 A1 | 1/2012 | Woodruff et al. |
| 2012/0059289 A1 | 3/2012 | Nield et al. |
| 2012/0065628 A1 | 3/2012 | Naito |
| 2012/0071863 A1 | 3/2012 | Lee et al. |
| 2012/0078139 A1 | 3/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078278 A1 | 3/2012 | Bales, Jr. et al. |
| 2012/0080332 A1 | 4/2012 | Shelton, IV et al. |
| 2012/0101495 A1 | 4/2012 | Young et al. |
| 2012/0116379 A1 | 5/2012 | Yates et al. |
| 2012/0116391 A1 | 5/2012 | Houser et al. |
| 2012/0116394 A1 | 5/2012 | Timm et al. |
| 2012/0116395 A1 | 5/2012 | Madan et al. |
| 2012/0130256 A1 | 5/2012 | Buysse et al. |
| 2012/0130365 A1 | 5/2012 | McLawhorn |
| 2012/0136354 A1 | 5/2012 | Rupp |
| 2012/0138660 A1 | 6/2012 | Shelton, IV |
| 2012/0143211 A1 | 6/2012 | Kishi |
| 2012/0150170 A1 | 6/2012 | Buysse et al. |
| 2012/0165816 A1 | 6/2012 | Kersten et al. |
| 2012/0172873 A1 | 7/2012 | Artale et al. |
| 2012/0172904 A1 | 7/2012 | Muir et al. |
| 2012/0177005 A1 | 7/2012 | Liang et al. |
| 2012/0184946 A1 | 7/2012 | Price et al. |
| 2012/0199630 A1 | 8/2012 | Shelton, IV |
| 2012/0199632 A1 | 8/2012 | Spivey et al. |
| 2012/0203143 A1 | 8/2012 | Sanai et al. |
| 2012/0203247 A1 | 8/2012 | Shelton, IV et al. |
| 2012/0209289 A1 | 8/2012 | Duque et al. |
| 2012/0209303 A1 | 8/2012 | Frankhouser et al. |
| 2012/0210223 A1 | 8/2012 | Eppolito |
| 2012/0215220 A1 | 8/2012 | Manzo et al. |
| 2012/0245582 A1 | 9/2012 | Kimball et al. |
| 2012/0253370 A1 | 10/2012 | Ross et al. |
| 2012/0265196 A1 | 10/2012 | Turner et al. |
| 2012/0269676 A1 | 10/2012 | Houser et al. |
| 2012/0310262 A1 | 12/2012 | Messerly et al. |
| 2012/0330307 A1 | 12/2012 | Ladtkow et al. |
| 2013/0012957 A1 | 1/2013 | Shelton, IV et al. |
| 2013/0012970 A1 | 1/2013 | Houser |
| 2013/0030433 A1 | 1/2013 | Heard |
| 2013/0035680 A1 | 2/2013 | Ben-Haim et al. |
| 2013/0053840 A1 | 2/2013 | Krapohl et al. |
| 2013/0072856 A1 | 3/2013 | Frankhouser et al. |
| 2013/0072857 A1 | 3/2013 | Frankhouser et al. |
| 2013/0079762 A1 | 3/2013 | Twomey et al. |
| 2013/0103023 A1 | 4/2013 | Monson et al. |
| 2013/0103024 A1 | 4/2013 | Monson et al. |
| 2013/0110145 A1 | 5/2013 | Weitzman |
| 2013/0123776 A1 | 5/2013 | Monson et al. |
| 2013/0123777 A1 | 5/2013 | Monson et al. |
| 2013/0123782 A1 | 5/2013 | Trees et al. |
| 2013/0123822 A1 | 5/2013 | Wellman et al. |
| 2013/0131660 A1 | 5/2013 | Monson et al. |
| 2013/0165929 A1 | 6/2013 | Muir et al. |
| 2013/0211397 A1 | 8/2013 | Parihar et al. |
| 2013/0217967 A1 | 8/2013 | Mohr et al. |
| 2013/0226207 A1 | 8/2013 | Stulen et al. |
| 2013/0226208 A1 | 8/2013 | Wiener et al. |
| 2013/0245659 A1 | 9/2013 | Robertson et al. |
| 2013/0267975 A1 | 10/2013 | Timm et al. |
| 2013/0274734 A1 | 10/2013 | Maass et al. |
| 2013/0282003 A1 | 10/2013 | Messerly et al. |
| 2013/0282038 A1 | 10/2013 | Dannaher et al. |
| 2013/0282039 A1 | 10/2013 | Wiener et al. |
| 2013/0285758 A1 | 10/2013 | Aldridge et al. |
| 2013/0289591 A1 | 10/2013 | Boudreaux et al. |
| 2013/0296908 A1 | 11/2013 | Schulte et al. |
| 2013/0338661 A1 | 12/2013 | Behnke, II |
| 2013/0345733 A1 | 12/2013 | Robertson et al. |
| 2014/0005640 A1 | 1/2014 | Shelton, IV et al. |
| 2014/0005653 A1 | 1/2014 | Shelton, IV et al. |
| 2014/0005654 A1 | 1/2014 | Batross et al. |
| 2014/0005656 A1 | 1/2014 | Mucilli et al. |
| 2014/0005661 A1 | 1/2014 | Shelton, IV et al. |
| 2014/0005662 A1 | 1/2014 | Shelton, IV et al. |
| 2014/0005667 A1 | 1/2014 | Stulen et al. |
| 2014/0005668 A1 | 1/2014 | Rhee et al. |
| 2014/0005676 A1 | 1/2014 | Shelton, IV et al. |
| 2014/0005680 A1 | 1/2014 | Shelton, IV et al. |
| 2014/0005681 A1 | 1/2014 | Gee et al. |
| 2014/0005682 A1 | 1/2014 | Worrell et al. |
| 2014/0005701 A1 | 1/2014 | Olson et al. |
| 2014/0005702 A1 | 1/2014 | Timm et al. |
| 2014/0005703 A1 | 1/2014 | Stulen et al. |
| 2014/0005704 A1 | 1/2014 | Vakharia et al. |
| 2014/0005705 A1 | 1/2014 | Weir et al. |
| 2014/0005708 A1 | 1/2014 | Shelton, IV et al. |
| 2014/0005718 A1 | 1/2014 | Shelton, IV et al. |
| 2014/0012299 A1 | 1/2014 | Stoddard et al. |
| 2014/0058427 A1 | 2/2014 | Robertson |
| 2014/0066962 A1 | 3/2014 | Robertson et al. |
| 2014/0087569 A1 | 3/2014 | Lee |
| 2014/0107538 A1 | 4/2014 | Wiener et al. |
| 2014/0114327 A1 | 4/2014 | Boudreaux et al. |
| 2014/0135804 A1 | 5/2014 | Weisenburgh, II et al. |
| 2014/0155921 A1 | 6/2014 | Price et al. |
| 2014/0180280 A1 | 6/2014 | Sigmon, Jr. |
| 2014/0243864 A1 | 8/2014 | Voegele et al. |
| 2014/0276738 A1 | 9/2014 | Price et al. |
| 2014/0276970 A1 | 9/2014 | Messerly et al. |
| 2014/0336686 A1 | 11/2014 | Houser et al. |
| 2015/0045819 A1 | 2/2015 | Houser et al. |
| 2015/0066067 A1 | 3/2015 | Stulen |
| 2015/0073460 A1 | 3/2015 | Stulen |
| 2015/0112335 A1 | 4/2015 | Boudreaux et al. |
| 2015/0119914 A1 | 4/2015 | Neurohr et al. |
| 2015/0119915 A1 | 4/2015 | Neurohr et al. |
| 2015/0119916 A1 | 4/2015 | Dietz et al. |
| 2015/0123348 A1 | 5/2015 | Robertson et al. |
| 2015/0157355 A1 | 6/2015 | Price et al. |
| 2015/0157356 A1 | 6/2015 | Gee |
| 2015/0164533 A1 | 6/2015 | Felder et al. |
| 2015/0164534 A1 | 6/2015 | Felder et al. |

(56) References Cited

U.S. PATENT DOCUMENTS

| | | | |
|---|---|---|---|
| 2015/0164535 A1 | 6/2015 | Felder et al. | |
| 2015/0164536 A1 | 6/2015 | Czarnecki et al. | |
| 2015/0164537 A1 | 6/2015 | Cagle et al. | |
| 2015/0164538 A1 | 6/2015 | Aldridge et al. | |

FOREIGN PATENT DOCUMENTS

| | | | |
|---|---|---|---|
| CN | 1253485 A | 5/2000 |
| CN | 1634601 A | 7/2005 |
| CN | 1640365 A | 7/2005 |
| CN | 1694649 A | 11/2005 |
| CN | 1922563 A | 2/2007 |
| CN | 1951333 A | 4/2007 |
| CN | 101040799 A | 9/2007 |
| CN | 101467917 A | 1/2009 |
| DE | 3904558 A1 | 8/1990 |
| DE | 9210327 U1 | 11/1992 |
| DE | 4323585 A1 | 1/1995 |
| DE | 19608716 C1 | 4/1997 |
| DE | 20021619 U1 | 3/2001 |
| DE | 10042606 A1 | 8/2001 |
| EP | 0136855 B1 | 9/1984 |
| EP | 0171967 A2 | 2/1986 |
| EP | 1839599 A1 | 10/1987 |
| EP | 0336742 A2 | 4/1989 |
| EP | 0424685 B1 | 5/1991 |
| EP | 0443256 A1 | 8/1991 |
| EP | 0456470 A1 | 11/1991 |
| EP | 0598976 A2 | 1/1994 |
| EP | 0677275 A2 | 3/1995 |
| EP | 0482195 B1 | 1/1996 |
| EP | 0695535 A1 | 2/1996 |
| EP | 0741996 A2 | 11/1996 |
| EP | 0612570 B1 | 6/1997 |
| EP | 1108394 A2 | 6/2001 |
| EP | 0908148 B1 | 1/2002 |
| EP | 1229515 A2 | 8/2002 |
| EP | 1285634 A1 | 2/2003 |
| EP | 0908155 B1 | 6/2003 |
| EP | 0705570 B1 | 4/2004 |
| EP | 0765637 B1 | 7/2004 |
| EP | 0870473 B1 | 9/2005 |
| EP | 0624346 B1 | 11/2005 |
| EP | 1594209 A1 | 11/2005 |
| EP | 1199044 B1 | 12/2005 |
| EP | 1609428 A1 | 12/2005 |
| EP | 1199043 B1 | 3/2006 |
| EP | 1433425 B1 | 6/2006 |
| EP | 1256323 B1 | 9/2006 |
| EP | 1704824 A1 | 9/2006 |
| EP | 1749479 A1 | 2/2007 |
| EP | 1815950 A1 | 8/2007 |
| EP | 1844720 A1 | 10/2007 |
| EP | 1862133 A1 | 12/2007 |
| EP | 1875875 A1 | 1/2008 |
| EP | 1199045 B1 | 6/2008 |
| EP | 1964530 A1 | 9/2008 |
| EP | 1972264 A1 | 9/2008 |
| EP | 1974771 A1 | 10/2008 |
| EP | 1435852 B1 | 12/2008 |
| EP | 1498082 B1 | 12/2008 |
| EP | 1707131 B1 | 12/2008 |
| EP | 1997438 A2 | 12/2008 |
| EP | 1477104 B1 | 1/2009 |
| EP | 2014218 A2 | 1/2009 |
| EP | 2042112 A2 | 4/2009 |
| EP | 1832259 B1 | 6/2009 |
| EP | 2074959 A1 | 7/2009 |
| EP | 2106758 A1 | 10/2009 |
| EP | 2111813 A1 | 10/2009 |
| EP | 2200145 A1 | 6/2010 |
| EP | 1214913 B1 | 7/2010 |
| EP | 2238938 A1 | 10/2010 |
| EP | 2298154 A2 | 3/2011 |
| EP | 1510178 B1 | 6/2011 |
| EP | 2305144 A1 | 6/2011 |
| EP | 2335630 A1 | 6/2011 |
| EP | 1502551 B1 | 7/2011 |
| EP | 2361562 A1 | 8/2011 |
| EP | 2365608 A2 | 9/2011 |
| EP | 2422721 A2 | 2/2012 |
| EP | 1927321 B1 | 4/2012 |
| EP | 2510891 A1 | 10/2012 |
| EP | 2316359 B1 | 3/2013 |
| EP | 1586275 B1 | 5/2013 |
| EP | 1616529 B1 | 9/2013 |
| EP | 2583633 B1 | 10/2014 |
| GB | 2032221 A | 4/1980 |
| GB | 2317566 A | 4/1998 |
| GB | 2379878 B | 11/2004 |
| GB | 2447767 B | 8/2011 |
| JP | S 50-100891 | 12/1973 |
| JP | S 59-68513 | 10/1982 |
| JP | 62-221343 A | 9/1987 |
| JP | S 62-227343 | 10/1987 |
| JP | 62-292153 A | 12/1987 |
| JP | 63-109386 A | 5/1988 |
| JP | 63-315049 A | 12/1988 |
| JP | H 01-151452 A | 6/1989 |
| JP | H 01-198540 A | 8/1989 |
| JP | 02-71510 U | 5/1990 |
| JP | 2-286149 A | 11/1990 |
| JP | H 02-292193 A | 12/1990 |
| JP | 04-25707 U | 2/1992 |
| JP | 4-30508 U | 3/1992 |
| JP | H 04-150847 A | 5/1992 |
| JP | H 04-152942 A | 5/1992 |
| JP | 05-095955 A | 4/1993 |
| JP | H 06-070938 A | 3/1994 |
| JP | 6-104503 A | 4/1994 |
| JP | 6-507081 A | 8/1994 |
| JP | H 7-508910 A | 10/1995 |
| JP | 7-308323 A | 11/1995 |
| JP | 8-24266 A | 1/1996 |
| JP | 8-275951 A | 10/1996 |
| JP | H 08-299351 A | 11/1996 |
| JP | H 08-336545 A | 12/1996 |
| JP | H 09-503146 A | 3/1997 |
| JP | H 09-135553 A | 5/1997 |
| JP | H 10-005237 A | 1/1998 |
| JP | 10-295700 A | 11/1998 |
| JP | H 11-501543 A | 2/1999 |
| JP | H 11-128238 | 5/1999 |
| JP | H 11-192235 | 7/1999 |
| JP | 11-253451 A | 9/1999 |
| JP | H 11-318918 A | 11/1999 |
| JP | 2000-041991 | 2/2000 |
| JP | 2000-070279 A | 3/2000 |
| JP | 2000-210299 A | 8/2000 |
| JP | 2000-287987 A | 10/2000 |
| JP | 2001-029353 A | 2/2001 |
| JP | 2001-502216 A | 2/2001 |
| JP | 2003612 A | 6/2001 |
| JP | 2001-309925 A | 11/2001 |
| JP | 2002-186901 A | 7/2002 |
| JP | 2002-204808 A | 7/2002 |
| JP | 2002-263579 A | 9/2002 |
| JP | 2002-301086 A | 10/2002 |
| JP | 2002-330977 A | 11/2002 |
| JP | 2002-542690 A | 12/2002 |
| JP | 2003-000612 A | 1/2003 |
| JP | 2003-010201 | 1/2003 |
| JP | 2003-510158 A | 3/2003 |
| JP | 2003-116870 A | 4/2003 |
| JP | 2003-126110 A | 5/2003 |
| JP | 2003-310627 A | 5/2003 |
| JP | 2003-530921 A | 10/2003 |
| JP | 2003-339730 A | 12/2003 |
| JP | 2004-147701 A | 5/2004 |
| JP | 2005027026 A | 1/2005 |
| JP | 2005-040222 A | 2/2005 |
| JP | 2005-066316 A | 3/2005 |
| JP | 2005-074088 A | 3/2005 |
| JP | 2005-534451 A | 11/2005 |

(56) References Cited

FOREIGN PATENT DOCUMENTS

| | | |
|---|---|---|
| JP | 2006-6410 A | 1/2006 |
| JP | 2006-512149 A | 4/2006 |
| JP | 2006-116194 A | 5/2006 |
| JP | 2006-158525 A | 6/2006 |
| JP | 2006-218296 A | 8/2006 |
| JP | 2006217716 A | 8/2006 |
| JP | 2006-288431 A | 10/2006 |
| JP | 2007-050181 A | 3/2007 |
| JP | 2003-126104 A | 5/2007 |
| JP | 2007-229454 A | 9/2007 |
| JP | 2007-527747 A | 10/2007 |
| JP | 2008-508065 A | 3/2008 |
| JP | 2008-119250 A | 5/2008 |
| JP | 2008-521503 A | 6/2008 |
| JP | 2008-212679 A | 9/2008 |
| JP | 2008-284374 | 11/2008 |
| JP | 2009-511206 A | 3/2009 |
| JP | 2009-517181 A | 4/2009 |
| JP | 4262923 B2 | 5/2009 |
| JP | 2009-523567 A | 6/2009 |
| JP | 2009-236177 | 10/2009 |
| JP | 2010-000336 A | 1/2010 |
| JP | 2010-514923 A | 5/2010 |
| JP | 2010-540186 A | 12/2010 |
| JP | 2012-235658 A | 11/2012 |
| JP | 5208761 B2 | 6/2013 |
| RU | 2154437 C1 | 8/2000 |
| WO | WO 92/22259 A2 | 12/1992 |
| WO | WO 93/08757 | 5/1993 |
| WO | WO 93/14708 A1 | 8/1993 |
| WO | WO 93/16646 | 9/1993 |
| WO | WO 93/20877 | 10/1993 |
| WO | WO 94/21183 A1 | 9/1994 |
| WO | WO 94/24949 | 11/1994 |
| WO | WO 95/09572 A1 | 4/1995 |
| WO | WO 96/30885 A1 | 10/1996 |
| WO | WO 96/39086 | 12/1996 |
| WO | WO 98/16156 | 4/1998 |
| WO | WO 98/026739 A1 | 6/1998 |
| WO | WO 98/35621 A1 | 8/1998 |
| WO | WO 98/37815 A1 | 9/1998 |
| WO | WO 98/47436 A1 | 10/1998 |
| WO | WO 99/20213 | 4/1999 |
| WO | WO 99/52489 | 10/1999 |
| WO | WO 00/64358 | 11/2000 |
| WO | WO 0074585 A2 | 12/2000 |
| WO | WO 01/54590 A1 | 8/2001 |
| WO | WO 01/67970 A1 | 9/2001 |
| WO | WO 01/95810 A2 | 12/2001 |
| WO | WO 02/24080 A2 | 3/2002 |
| WO | WO 02/38057 A1 | 5/2002 |
| WO | WO 02/062241 A1 | 8/2002 |
| WO | WO 03/082133 A1 | 10/2003 |
| WO | WO 2004/012615 A1 | 2/2004 |
| WO | WO 2004/026104 A2 | 4/2004 |
| WO | WO 2004/032754 A2 | 4/2004 |
| WO | WO 2004/032762 A1 | 4/2004 |
| WO | WO 2004/032763 A2 | 4/2004 |
| WO | WO 2004/037095 A2 | 5/2004 |
| WO | WO 2004/098426 A1 | 11/2004 |
| WO | WO 2004/112618 A2 | 12/2004 |
| WO | WO 2005/117735 A1 | 12/2005 |
| WO | WO 2005/122917 A1 | 12/2005 |
| WO | WO 2006/012797 A1 | 2/2006 |
| WO | WO 2006/042210 A2 | 4/2006 |
| WO | WO 2006/058223 A2 | 6/2006 |
| WO | WO 2006/063199 A2 | 6/2006 |
| WO | WO 2006/083988 A1 | 8/2006 |
| WO | WO 2006/119139 A2 | 11/2006 |
| WO | WO 2006/119376 | 11/2006 |
| WO | WO 2006/129465 A1 | 12/2006 |
| WO | WO 2007/008703 A2 | 1/2007 |
| WO | WO 2007/008710 A2 | 1/2007 |
| WO | WO 2007/040818 A1 | 4/2007 |
| WO | WO 2007/047380 A2 | 4/2007 |
| WO | WO 2007/047531 A2 | 4/2007 |
| WO | WO 2007/056590 A1 | 5/2007 |
| WO | WO 2007/087272 A2 | 8/2007 |
| WO | WO 2007/143665 A2 | 12/2007 |
| WO | WO 2008/016886 A2 | 2/2008 |
| WO | WO 2008/042021 A1 | 4/2008 |
| WO | WO 2008/049084 A2 | 4/2008 |
| WO | WO 2008/051764 A2 | 5/2008 |
| WO | WO 2008/089174 A2 | 7/2008 |
| WO | WO 2008/118709 A1 | 10/2008 |
| WO | WO 2008/130793 A1 | 10/2008 |
| WO | WO 2009/010565 A1 | 1/2009 |
| WO | WO 2009/018406 A2 | 2/2009 |
| WO | WO 2009/027065 A1 | 3/2009 |
| WO | WO 2009/046234 A2 | 4/2009 |
| WO | WO 2009/120992 A2 | 10/2009 |
| WO | WO 2010/068783 A1 | 6/2010 |
| WO | WO 2011/008672 A2 | 1/2011 |
| WO | WO 2011/052939 A2 | 5/2011 |
| WO | WO 2011/100321 A2 | 8/2011 |
| WO | WO 2011/144911 A1 | 11/2011 |
| WO | WO 2012/061722 A2 | 5/2012 |
| WO | WO 2012/128362 A1 | 9/2012 |
| WO | WO 2012/135705 A1 | 10/2012 |
| WO | WO 2012/135721 A1 | 10/2012 |
| WO | WO 2013/018934 A1 | 2/2013 |
| WO | WO 2013/062978 A2 | 5/2013 |

OTHER PUBLICATIONS

Technology Overview, printed from www.harmonicscalpel.com, Internet site, website accessed on Jun. 13, 2007, (3 pages).

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.

AST Products, Inc., "Principles of Video Contact Angle Analysis," 20 pages, (2006).

Lim et al., "A Review of Mechanism Used in Laparoscopic Surgical Instruments," Mechanism and Machine Theory, vol. 38, pp. 1133-1147, (2003).

Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).

Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).

Incropera et al., "Fundamentals of Heat and Mass Transfer", Wiley, New York (1990). (Book—not attached).

F. A. Duck, "Optical Properties of Tissue Including Ultraviolet and Infrared Radiation," pp. 43-71 in *Physical Properties of Tissue* (1990).

Orr et al., "Overview of Bioheat Transfer," pp. 367-384 in Optical-Thermal Response of Laser-Irradiated Tissue, A. J. Welch and M. J. C. van Gemert, eds., Plenum, New York (1995).

Campbell et al, "Thermal Imaging in Surgery," p. 19-3, in *Medical Infrared Imaging*, N. A. Diakides and J. D. Bronzino, Eds. (2008).

Sullivan, "Cost-Constrained Selection of Strand Diameter and Number in a Litz-Wire Transformer Winding," IEEE Transactions on Power Electronics, vol. 16, No. 2, Mar. 2001, pp. 281-288.

Sullivan, "Optimal Choice for Number of Strands in a Litz-Wire Transformer Winding," IEEE Transactions on Power Electronics, vol. 14, No. 2, Mar. 1999, pp. 283-291.

Graff, K.F., "Elastic Wave Propagation in a Curved Sonic Transmission Line," IEEE Transactions on Sonics and Ultrasonics, SU-17(1), 1-6 (1970).

Makarov, S. N., Ochmann, M., Desinger, K., "The longitudinal vibration response of a curved fiber used for laser ultrasound surgical therapy," Journal of the Acoustical Society of America 102, 1191-1199 (1997).

Morley, L. S. D., "Elastic Waves in a Naturally Curved Rod," Quarterly Journal of Mechanics and Applied Mathematics, 14: 155-172 (1961).

(56) References Cited

OTHER PUBLICATIONS

Walsh, S. J., White, R. G., "Vibrational Power Transmission in Curved Beams," Journal of Sound and Vibration, 233(3), 455-488 (2000).
http://www.apicalinstr.com/generators.htm.
http://www.dotmed.com/listing/electrosurical-unit/ethicon/ultracision-g110-/1466724.
http:/www.ethicon.com/gb-en/healthcare-professionals/products/energy-devices/capital//ge . . . .
http://www.4-traders.com/JOHNSON-JOHNSON-4832/news/Johnson-Johnson-Ethicon-E . . .
http://www.medicalexpo.com/medical-manufacturer/electrosurgical-generator-6951.html.
http://www.meqadyne.com/es_generator.php.
http://www.valleylab.com/product/es/generators/index.html.
Covidien 501(k) Summary Sonicision, dated Feb. 24, 2011 (7 pages).
Gerhard, Glen C., "Surgical Electrotechnology: Quo Vadis?," Biomedical Engineering, IEEE Transactions on , vol. BME-31, No. 12, pp. 787, 792, Dec. 1984.
Fowler, K.R., "A programmable, arbitrary waveform electrosurgical device," Engineering in Medicine and Biology Society, 1988. Proceedings of the Annual International Conference of the IEEE, vol., No., pp. 1324, 1325 vol. 3, Nov. 4-7, 1988.
LaCourse, J.R.; Vogt, M.C.; Miller, W.T., III; Selikowitz, S.M., "Spectral analysis interpretation of electro-surgical generator nerve and muscle stimulation," Biomedical Engineering, IEEE Transactions on , vol. 35, No. 7, pp. 505, 509, Jul. 1988.
U.S. Appl. No. 13/751,680, filed Jan. 28, 2013.

\* cited by examiner

MEDICAL DEVICE

This application is a U.S. national stage application of and claims the priority benefit of PCT/GB2011/000778 filed on May 20, 2011.

BACKGROUND

The present invention relates to the field of medical devices and in particular, although not exclusively, to medical cauterization and cutting devices. The invention also relates to drive circuits and methods for driving such medical devices.

Many surgical procedures require cutting or ligating blood vessels or other internal tissue. Many surgical procedures are performed using minimally invasive techniques, a hand-held cauterization device is used by the surgeon to perform the cutting or ligating. The existing hand-held cauterization devices require a desk top power supply and control electronics that are connected to the device through an electrical supply line. FIG. 10 illustrates such an existing hand-held cauterization device currently in use.

It has been known for a number of years that these existing devices are cumbersome and difficult to use during a surgical operation due to the large size of the supply and control electronics and due to the tethering of the hand-held cauterization device to the supply and control electronics. It has also been known for a number of years that these problems would be overcome by providing a battery powered hand-held cauterization device in which the power and control electronics are mounted within the device itself, such as within the handle of the device. However, it is not a simple matter of miniaturising the electronics. The power that has to be supplied to the device during the surgical procedure and the current design of the electronics is such that large capacitors, inductors and transformers as well as heat sinks and fans are required. FIG. 11 illustrates in more detail the different parts of the supply and control electronics that are used in the existing design as illustrated in FIG. 10. Whilst it is possible to reduce the size of the sensing and control electronics, other parts of the circuitry cannot be miniaturised in this way.

In particular, the existing electronics design uses circuitry for providing an adjustable 24 Volt power supply; FETs and associated drive circuitry; a transformer for increasing the supply voltage; and filtering circuitry to remove harmonics from the square wave voltage levels that are generated by the FEE switches and the transformer. Given the voltage levels and the power levels used to drive the cauterization device, the transformers and output filters all have to be relatively bulky devices and large heat sinks and a fan are required to cool the FET switches.

The present invention aims to provide an alternative circuit design that will allow the miniaturisation of the circuitry so that it can be built into the hand-held cauterization device, whilst still being able to provide the power and control required for the medical procedure.

SUMMARY

The present invention provides a medical device comprising an end effector having at least one electrical contact a radio frequency, RF, generation circuit for generating an RF drive signal and to provide the RF drive signal to the at least one electrical contact and wherein the RF generation circuit comprises a resonant circuit. In one embodiment, the radio frequency generation circuit comprises switching circuitry that generates a cyclically varying signal, such as a square wave signal, from a DC supply and the resonant circuit is configured to receive the cyclically varying signal from the switching circuitry. The DC supply is preferably provided by one or more batteries that can be mounted in a housing (such as a handle) of the device.

According to another aspect, the invention provides a medical device comprising: a handle for gripping by a user; an end effector coupled to the handle, the end effector having at least one electrical contact; battery terminals for connecting to one or more batteries; a radio frequency, RF, generation circuit coupled to said battery terminals and operable to generate an RF drive signal and to provide the RF drive signal to the at least one electrical contact of said end effector; wherein the frequency generation circuit comprises: switching circuitry for generating a cyclically varying signal (which may be a square wave pulse width modulated signal) from a potential difference across said battery terminals; and a resonant drive circuit coupled to said switching circuitry and operable to filter the cyclically varying signal generated by the switching circuitry; and wherein the RF drive signal is obtained using an output signal from said resonant circuit.

The medical device may also comprise a control circuit (which may comprise hardware and/or software) that varies the frequency of the RF drive signal. The control circuit may vary the frequency based on a measurement of the RF drive signal in order to control at least one of the power, voltage and/or current delivered to the at least one electrical contact of the end effector. In a preferred embodiment, the measurement is obtained from a sampling circuit that operates synchronously with respect to the frequency of the RF drive signal. The frequency at which the sampling circuit samples the sensed signal may be an integer fraction of the frequency of the RF drive signal.

In one embodiment, the control circuit varies the frequency of the RF drive signal around (preferably just above or just below) the resonant frequency of the resonant circuit. The resonant characteristic of the resonant circuit may vary with a load connected to the at least one electrical contact and the control circuit may be arranged to vary the RF drive frequency to track changes in the resonant characteristic of the resonant circuit.

According to another aspect, the invention provides a medical device comprising: a handle for gripping by a user; an end effector coupled to the handle and having at least one electrical contact; a radio frequency, RF, generation circuit operable to generate an RF drive signal and to provide the RF drive signal to the at least one electrical contact; and a control circuit operable to vary the frequency of the RF drive signal to control at least one of the power, the voltage and the current provided to the at least one contact of the end effector.

The RF generation circuit may comprise a signal generator that generates a cyclically varying signal at the RF frequency; and a frequency dependent attenuator that attenuates the cyclically varying signal in dependence upon the frequency of the cyclically varying signal. The frequency dependent attenuator may be a lossless attenuator and may comprise a resonant circuit having a resonant frequency at or near the RF frequency of the cyclically varying signal.

The present invention also provides a medical device comprising: a handle for gripping by a user; an end effector coupled to the handle and having at least one electrical contact; a radio frequency, RF, generation circuit operable to generate an RF drive signal and to provide the RF drive signal to the at least one electrical contact; an input for receiving a sensed signal that varies with the RF drive signal applied to the at least one electrical contact; a sampling circuit for sampling the sensed signal received at said input; a measurement circuit operable to make measurements of the RF drive signal using samples obtained from the sampling circuit; and a control circuit operable to control the RF generation circuit in dependence upon the measurements made by the measurement circuit, to vary the frequency of the generated RF drive signal; wherein the sampling circuit is operable to sample the sensed signal at a sampling frequency that varies in synchronism with the frequency of the RE drive signal.

The invention also provides a method of operating a medical device comprising generating an RF signal and applying the RF signal to at least one electrode of an end effector of the medical device and controlling the frequency of the generated RF signal to control at least one of the power, current, and voltage applied to the at least one electrode.

According to another aspect, the invention provides a method of cauterising a vessel or tissue, the method comprising: gripping the vessel or tissue with an end effector of a medical device; applying an RF signal to at least one electrode of the end effector that is in contact with the vessel or tissue; and controlling the frequency of the RF signal to control at least one of the power, current, and voltage applied to the tissue to perform the cauterisation.

The above methods may use the above described medical device, although that is not essential.

The controlling step may vary the frequency of the RF signal to control the power applied to the tissue or vessel, and the method may further comprise obtaining measurements of the impedance of the tissue or vessel and varying the desired power applied to the tissue or vessel in dependence upon the obtained impedance measurements.

FIGURES

These and various other features and aspects of the invention will become apparent from the following detailed description of embodiments which are described with reference to the accompanying Figures in which:

FIG. 5b illustrates a resulting power plot obtained by combining the current and voltage plots illustrated in FIG. 5a;

DETAILED DESCRIPTION

Medical Device

Many surgical procedures require cutting or ligating blood vessels or other vascular tissue. With minimally invasive surgery, surgeons perform surgical operations through a small incision in the patient's body. As a result of the limited space, surgeons often have difficulty controlling bleeding by clamping and/or tying-off transected blood vessels. By utilizing electrosurgical forceps, a surgeon can cauterize, coagulate/desiccate, and/or simply reduce or slow bleeding by controlling the electrosurgical energy applied through jaw members of the electrosurgical forceps.

Figure 1:
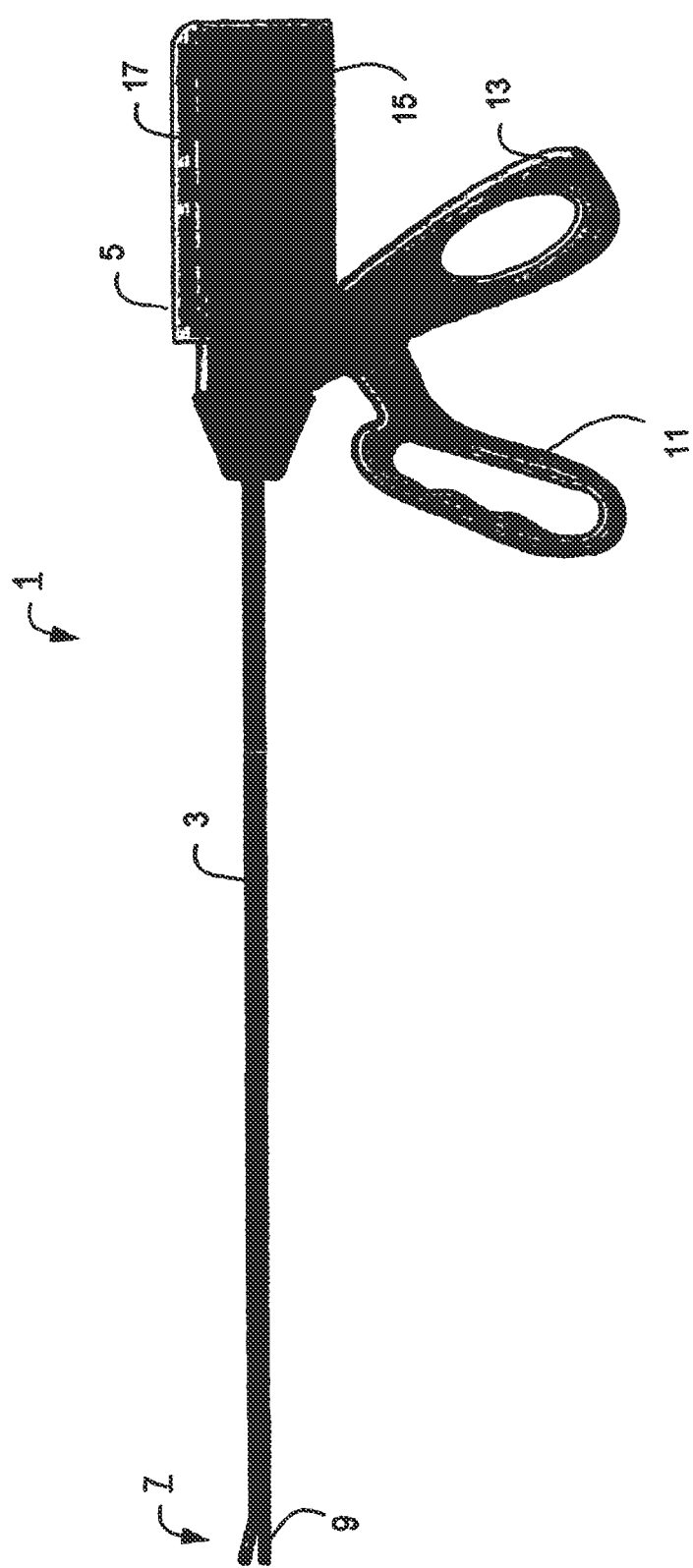
FIG. 1 illustrates a hand-held cauterization device that has batteries and drive and control circuitry mounted into a handle portion of the device.

FIG. 1 illustrates the form of an electrosurgical medical device 1 that is designed for minimally invasive medical procedures, according to one embodiment of the present invention. As shown, the device 1 is a self contained device, having an elongate shaft 3 that has a handle 5 connected to the proximal end of the shaft 3 and an end effector 7 connected to the distal end of the shaft 3. In this embodiment, the end effector 7 comprises medical forceps 9 and a cutting blade (not shown) that are controlled by the user manipulating control levers 11 and 13 of the handle 5.

During a surgical procedure, the shaft 3 is inserted through a trocar to gain access to the patient's interior and the operating site. The surgeon will manipulate the forceps 9 using the handle 5 and the control levers 11 and 13 until the forceps 9 are located around the vessel to be cauterised. Electrical energy at an RF frequency (it has been found that frequencies above about 50 kHz do not affect the human nervous system) is then applied, in a controlled manner, to the forceps 9 to perform the desired cauterisation. As shown in FIG. 1, in this embodiment, the handle 5 houses batteries 15 and control electronics 17 for generating and controlling the electrical energy required to perform the cauterisation. In this way, the device 1 is self contained in the sense that it does not need a separate control box and supply wire to provide the electrical energy to the forceps 9.

RF Drive Circuitry

Figure 2:
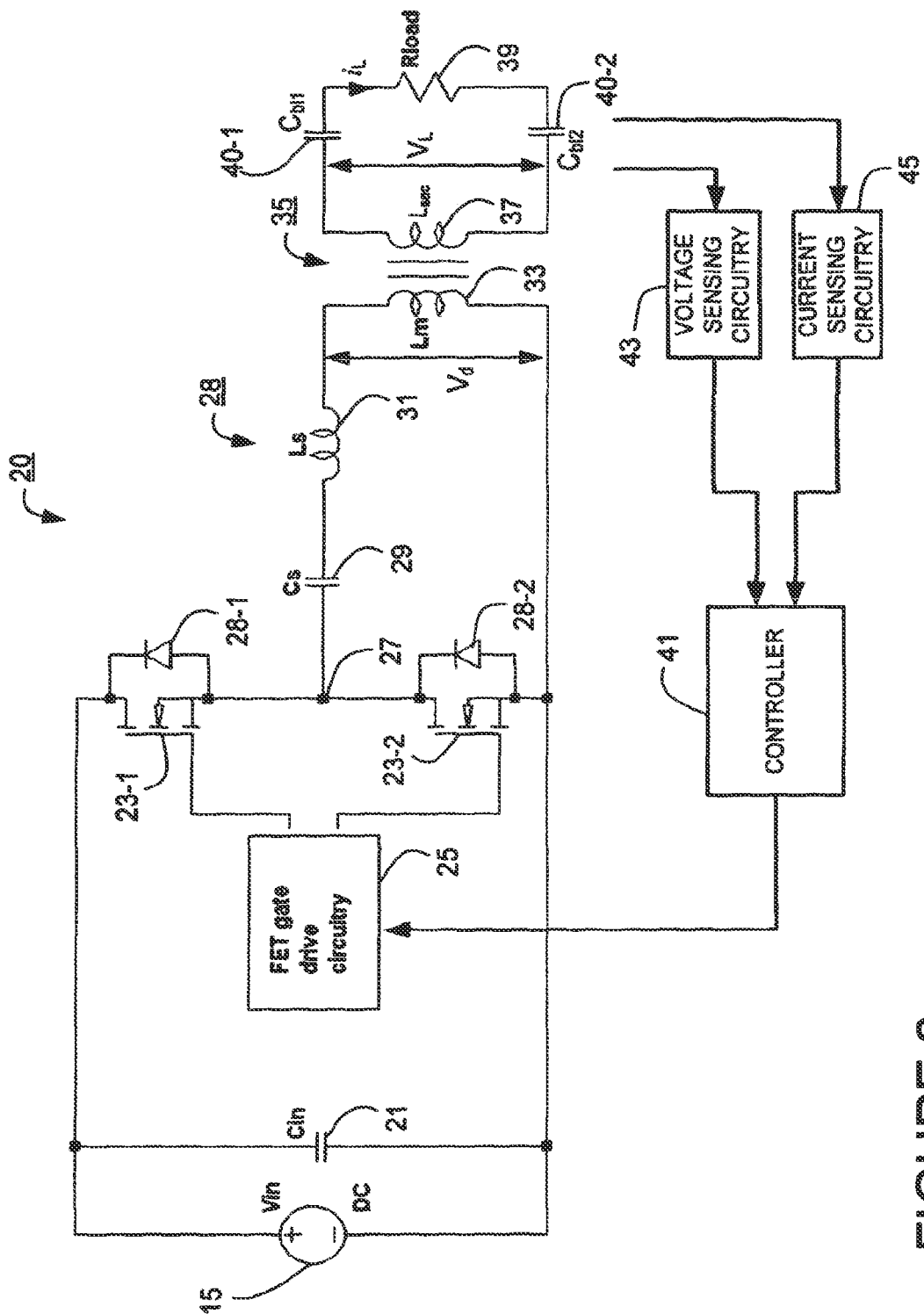
FIG. 2 is a part block part schematic diagram illustrating the main components of the RF drive circuitry and control circuitry used in one embodiment of the invention.

FIG. 2 is a part schematic part block diagram illustrating the RF drive and control circuitry 20 used in this embodiment to generate and control the RF electrical energy supplied to the forceps 9. As will be explained in more detail below, in this embodiment, the drive circuitry 20 is a resonant based circuit and the control circuitry operates to control the operating frequency of the drive signal so that it is varied around the resonant frequency of the drive circuit, which in turn controls the amount of power supplied to the forceps 9. The way that this is achieved will become apparent from the following description.

As shown in FIG. 2, the drive circuitry 20 comprises the above described batteries 15 that are arranged to supply, in this example, OV and 24V rails. An input capacitor ($C_{in}$) 21 is connected between the OV and the 24V rails for providing a low source impedance. A pair of FET switches 23-1 and 23-2 (both of which are N-channel in this embodiment to reduce power losses) is connected in series between the OV rail and the 24V rail. FET gate drive circuitry 25 is provided that generates two drive signals—one for driving each of the two FETs 23. The FET gate drive circuitry 25 generates drive signals that causes the upper FET (23-1) to be on when the lower FET (23-2) is off and vice versa. This causes the node 27 to be alternately connected to the 24V rail (when FET 23-1 is switched on) and the OV rail (when the FET 23-2 is switched on). FIG. 2 also shows the internal parasitic diodes 28-1 and 28-2 of the corresponding FETs 23, which conduct during any periods that the FETs 23 are open.

As shown in FIG. 2, the node 27 is connected to a capacitor-inductor-inductor resonant circuit 28 formed by capacitor $C_s$ 29, inductor $L_s$ 31 and inductor $L_m$ 33. The FET gate driving circuitry 25 is arranged to generate drive signals at a drive frequency ($f_d$) that opens and closes the FET switches 23 at around the resonant frequency of the resonant circuit 28. As a result of the resonant characteristic of the resonant circuit 28, the square wave voltage at node 27 will cause a substantially sinusoidal current at the drive frequency ($f_d$) to flow within the resonant circuit 28. As illustrated in FIG. 2, the inductor $L_m$ 33 is the primary of a transformer 35, the secondary of which is formed by inductor $L_{sec}$ 37. The transformer 35 up-converts the drive voltage ($V_d$) across inductor Lm 33 to the load voltage ($V_L$) that is applied to the load (represented by the load resistance $R_{load}$ 39 in FIG. 2) corresponding to the impedance of the forceps' jaws and any tissue or vessel gripped by the forceps 9. As shown in FIG. 2, a pair of DC blocking capacitors Cb. 40-1 and 40-2 is provided to prevent any DC signal being applied to the load 39.

In this embodiment, the amount of electrical power supplied to the forceps 9 is controlled by varying the frequency of the switching signals used to switch the FETs 23. This works because the resonant circuit 28 acts as a frequency dependent (lossless) attenuator. The closer the drive signal is to the resonant frequency of the resonant circuit 28, the less the drive signal is attenuated. Similarly, as the frequency of the drive signal is moved away from the resonant frequency of the circuit 28, the more the drive signal is attenuated and so the power supplied to the load reduces. In this embodiment, the frequency of the switching signals generated by the FET gate drive circuitry 25 is controlled by a controller 41 based on a desired power to be delivered to the load 39 and measurements of the load voltage ($V_L$) and of the load current ($i_L$) obtained by conventional voltage sensing circuitry 43 and current sensing circuitry 45. The way that the controller 41 operates will be described in more detail below.

Controller

Figure 3:
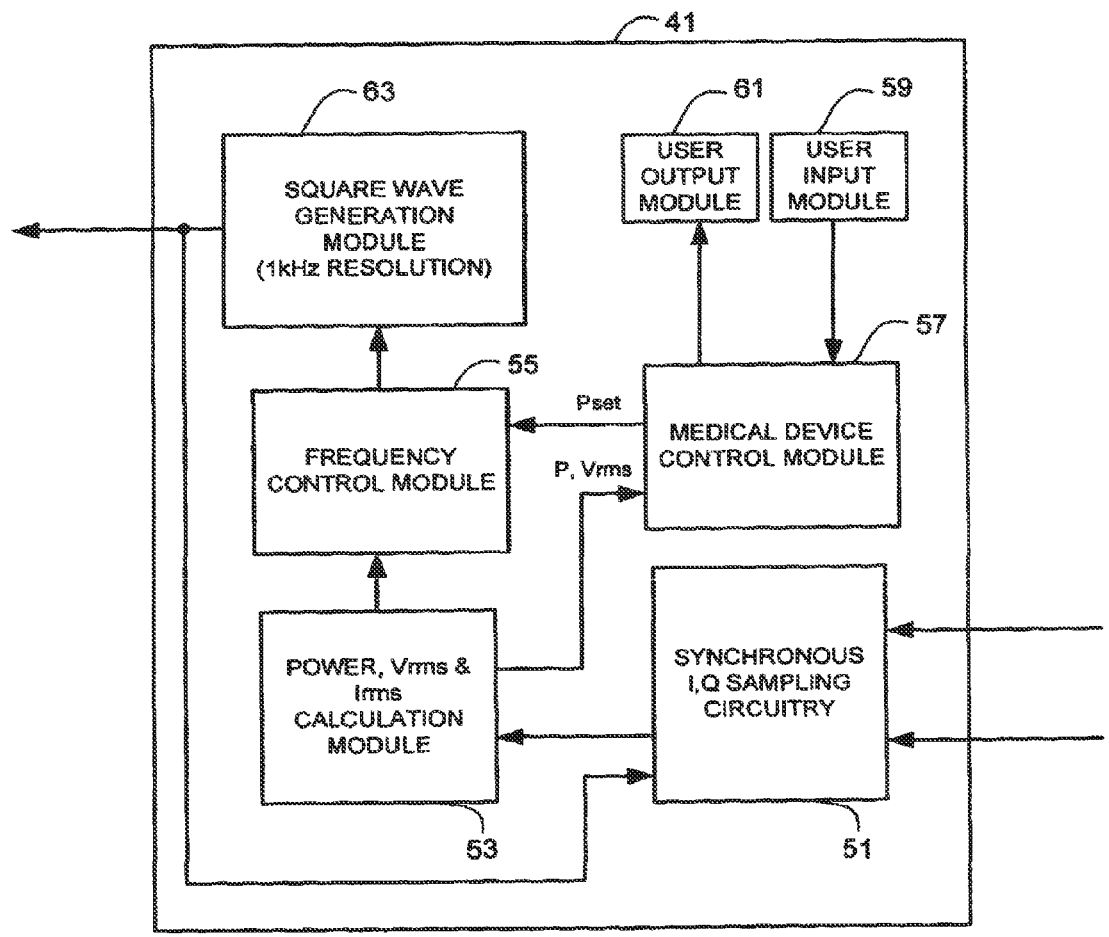
FIG. 3 is a block diagram illustrating the main components of a controller used to control the operation of the RF drive circuitry illustrated in FIG. 2.

FIG. 3 is a block diagram illustrating the main components of the controller 41. In this embodiment, the controller 41 is a micro-processor based controller and so most of the components illustrated in FIG. 3 are software based components. However, a hardware based controller 41 may be used instead. As shown, the controller 41 includes synchronous I,Q sampling circuitry 51 that receives the sensed voltage and current signals from the sensing circuitry 43 and 45 and obtains corresponding samples which are passed to a power, $V_{rms}$ and $I_{rms}$ calculation module 53. The calculation module 53 uses the received samples to calculate the RMS voltage and RMS current applied to the load 39 (forceps 9 and tissue/vessel gripped thereby) and from them the power that Is presently being supplied to the load 39. The determined values are then passed to a frequency control module 55 and a medical device control module 57. The medical device control module 57 uses the values to determine the present impedance of the load 39 and based on this determined impedance and a pre-defined algorithm, determines what set point power ($P_{set}$) should be applied to the frequency control module 55. The medical device control module 57 is in turn controlled by signals received from a user input module 59 that receives inputs from the user (for example pressing buttons or activating the control levers 11 or 13 on the handle 5) and also controls output devices (lights, a display, speaker or the like) on the handle 5 via a user output module 61.

The frequency control module 55 uses the values obtained from the calculation module 53 and the power set point ($P_{set}$) obtained from the medical device control module 57 and predefined system limits (to be explained below), to determine whether or not to increase or decrease the applied frequency. The result of this decision is then passed to a square wave generation module 63 which, in this embodiment, increments or decrements the frequency of a square wave signal that it generates by 1 kHz, depending on the received decision. As those skilled in the art will appreciate, in an alternative embodiment, the frequency control module 55 may determine not only whether to increase or decrease the frequency, but also the amount of frequency change required. In this case, the square wave generation module 63 would generate the corresponding square wave signal with the desired frequency shift. In this embodiment, the square wave signal generated by the square wave generation module 63 is output to the FET gate drive circuitry 25, which amplifies the signal and then applies it to the FET 23-1. The FET gate drive circuitry 25 also inverts the signal applied to the FET 23-1 and applies the inverted signal to the FET 23-2.

Drive Signals and Signal Measurements

Figure 4:
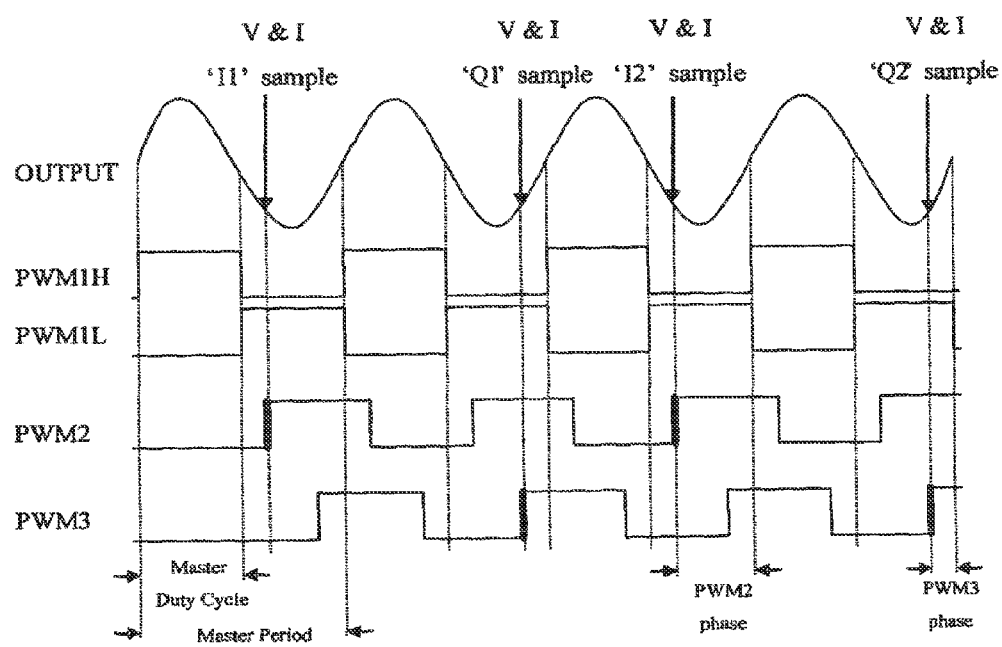
FIG. 4 is a timing diagram illustrating the RF drive signals applied to the cauterization device and illustrating a way in which synchronous samples may be obtained to measure the drive signals.

FIG. 4 is a signal plot illustrating the switching signals applied to the FETs 23; a sinusoidal signal representing the measured current or voltage applied to the load 39; and the timings when the synchronous sampling circuitry 51 samples the sensed load voltage and load current. In particular, FIG. 4 shows the switching signal (labelled PWM1H) applied to upper FET 23-1 and the switching signal (labelled PWM1L) applied to lower FET 23-2. Although not illustrated for simplicity, there is a dead time between PWM1H and PWM1L to ensure that that both FETs 23 are not on at the same time. FIG. 4 also shows the measured load voltage/current (labelled OUTPUT). Both the load voltage and the load current will be a sinusoidal waveform, although they may be out of phase, depending on the impedance of the load 39. As shown, the load current and load voltage are at the same drive frequency ($f_d$) as the switching signals (PWM1H and PWM1L) used to switch the FETs 23. Normally, when sampling a sinusoidal signal, it is necessary to sample the signal at a rate corresponding to at least twice the frequency of the signal being sampled—i.e. two samples per period. However, as the controller 41 knows the frequency of the switching signals, the synchronous sampling circuit 51 can sample the measured voltage/current signal at a lower rate. In this embodiment, the synchronous sampling circuit 51 samples the measured signal once per period, but at different phases in adjacent periods. In FIG. 4, this is illustrated by the "I" sample and the "Q" sample. The timing that the synchronous sampling circuit 51 makes these samples is controlled, in this embodiment, by the two control signals PWM2 and PWM3, which have a fixed phase relative to the switching signals (PWM1H and PWM1L) and are out of phase with each other (preferably by quarter of the period as this makes the subsequent calculations easier). As shown, the synchronous sampling circuit 51 obtains an "I" sample on every other rising edge of the PWM2 signal and the synchronous sampling circuit 51 obtains a "Q" sample on every other rising edge of the PWM3 signal. The synchronous sampling circuit 51 generates the PWM2 and PWM3 control signals from the square wave signal output by the square wave generator 63 (which is at the same frequency as the switching signals PWM1H and PWM1L). Thus when the frequency of the switching signals is changed, the frequency of the sampling control signals PWM2 and PWM3 also changes (whilst their relative phases stay the same). In this way, the sampling circuitry 51 continuously changes the timing at which it samples the sensed voltage and current signals as the frequency of the drive signal is changed so that the samples are always taken at the same time points within the period of the drive signal. Therefore, the sampling circuit 51 is performing a "synchronous" sampling operation Instead of a more conventional sampling operation that just samples the input signal at a fixed sampling rate defined by a fixed sampling clock.

The samples obtained by the synchronous sampling circuitry 51 are then passed to the power, $V_{rms}$ and $I_{rms}$ calculation module 53 which can determine the magnitude and phase of the measured signal from just one "I" sample and one "Q" sample of the load current and load voltage. However, in this embodiment, to achieve some averaging, the calculation module 53 averages consecutive "I" samples to provide an average "I" value and consecutive "0" samples to provide an average "Q" value; and then uses the average I and Q values to determine the magnitude and phase of the measured signal (in a conventional manner). As those skilled in the art will appreciate, with a drive frequency of about 400 kHz and sampling once per period means that the synchronous sampling circuit 51 will have a sampling rate of 400 kHz and the calculation module 53 will produce a voltage measure and a current measure every 0.01 ms. The operation of the synchronous sampling circuit 51 offers an improvement over existing products, where measurements can not be made at the same rate and where only magnitude information is available (the phase information being lost).

Limits

As with any system, there are certain limits that can be placed on the power, current and voltage that can be delivered to the forceps 9. The limits used in this embodiment and how they are controlled will now be described.

Figure 5A:
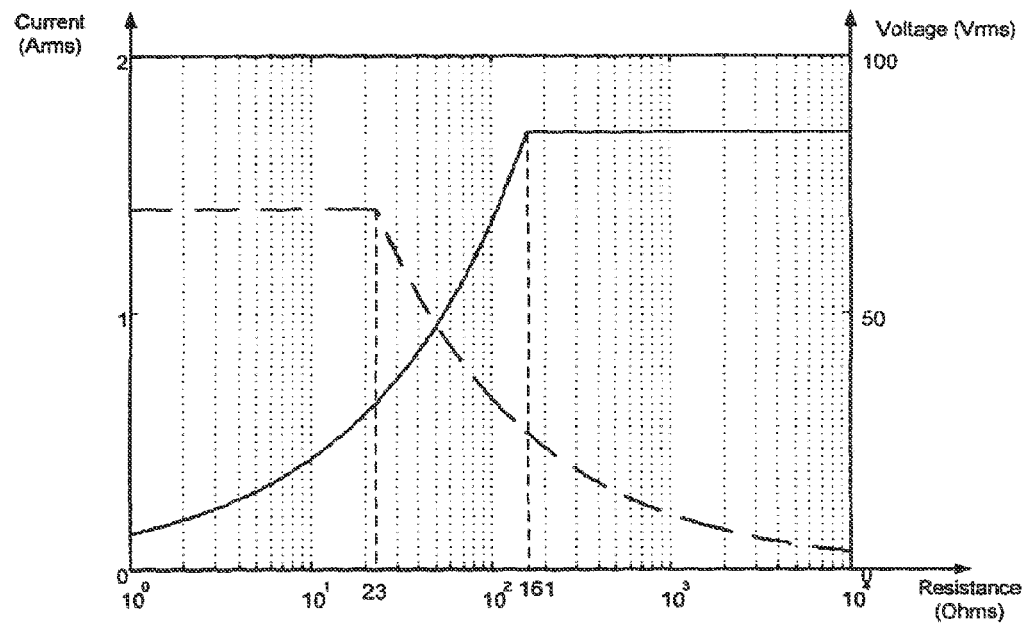
FIG. 5a is a plot illustrating limits that are placed on voltage and current supplied to the cauterization device illustrated in FIG. 1.
Figure 5B:
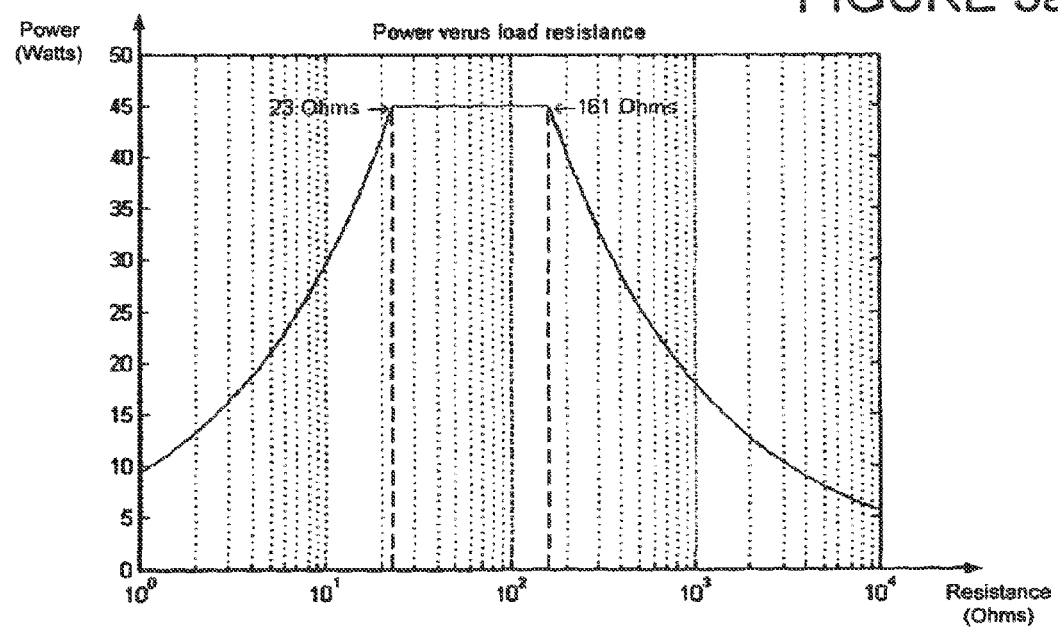

In this embodiment, the RF drive circuitry 20 is designed to deliver a power limited sine wave into tissue with the following requirements:
1) Supplied with a nominally 24V DC supply
2) Substantially sinusoidal output waveform at approximately 400 kHz
3) Power limited output of 45 W
4) Current limited to 1.4 $A_{rms}$ and voltage limited to 85$V_{rms}$ The last two requirements are represented graphically in FIGS. 5a and 5b. In particular, FIG. 5a illustrates idealised plots of voltage and current for loads between 1 Ohm and 10 k Ohms on a logarithmic scale; and FIG. 5b illustrates the power delivered to the load 39 for loads between 1 Ohm and 10 k Ohms.

The frequency control module 55 maintains data defining these limits and uses them to control the decision about whether to increase or decrease the excitation frequency.

Resonant Characteristic and Frequency Control

As mentioned above, the amount of electrical power supplied to the forceps 9 is controlled by varying the frequency of the switching signals used to switch the FETs 23. This is achieved by utilising the fact that the impedance of the resonant circuit 28 changes rapidly with frequency. Therefore by changing the frequency of the switching signals, the magnitude of the current through the resonant circuit 28, and hence through the load 39, can be varied as required to regulate the output power.

Figure 6:
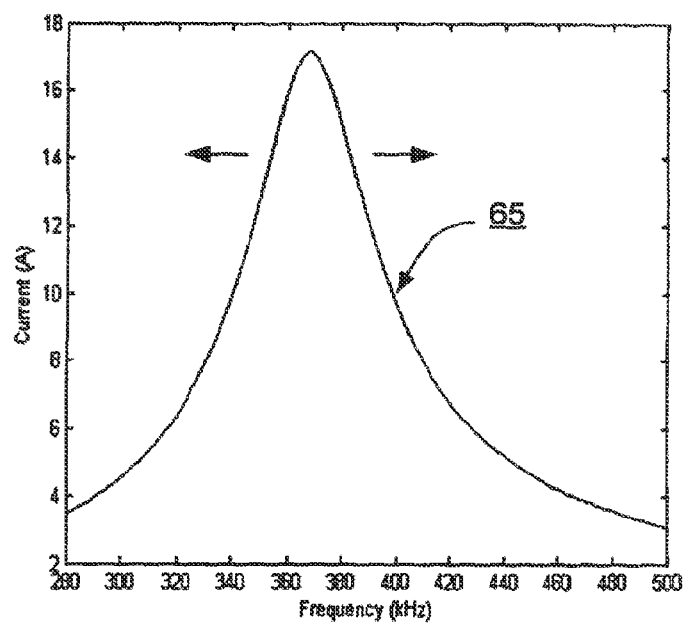
FIG. 6 is a plot illustrating the way in which the resonant characteristics of the RF drive circuit illustrated in FIG. 2 varies with different loads.

As those skilled in the art will appreciate, the resonant circuit 28 is coupled to a load 39 whose impedance will vary during the surgical procedure. Indeed the medical device control module 57 uses this variation to determine whether the tissue or vessel has been cauterised, coagulated/desiccated. The varying impedance of the load 39 changes the frequency characteristic of the RF drive circuit 20 and hence the current that flows through the resonant circuit 28. This is illustrated in FIG. 6, which is a plot 65 illustrating the way in which the current through the resonant circuit 28 varies with the drive frequency for a fixed value of load impedance. As the impedance of the load 39 increases, the resonant characteristic 65 will change shape (the peak may grow or reduce in height) and will move to the left and as the impedance of the load decreases it will change its shape and move to the right. Therefore, the frequency control module 55 must operate quickly enough to track the changes in the resonant characteristic 65. This is easily achievable in this embodiment, where power, current and voltage measurements are available every 0.01 ms. In general terms, measurements would only be required at a rate of about once every 0.1 s to track the changes. However sudden changes in the resonant characteristic 65 can occur, which the frequency control module 55 cannot track. When this happens, the frequency control module 55 resets the operating frequency to a value where it knows that it will be on one side of the characteristic.

As the impedance of the resonant circuit 28 increases sharply both above and below resonance, it is possible to operate the RF drive circuit 20 either above or below the resonant frequency. In this embodiment, the frequency control module 55 controls the operation of the drive circuit 20 so that it operates slightly above the resonant frequency as this should lead to lower switching losses through the FETs 23.

Figure 7:
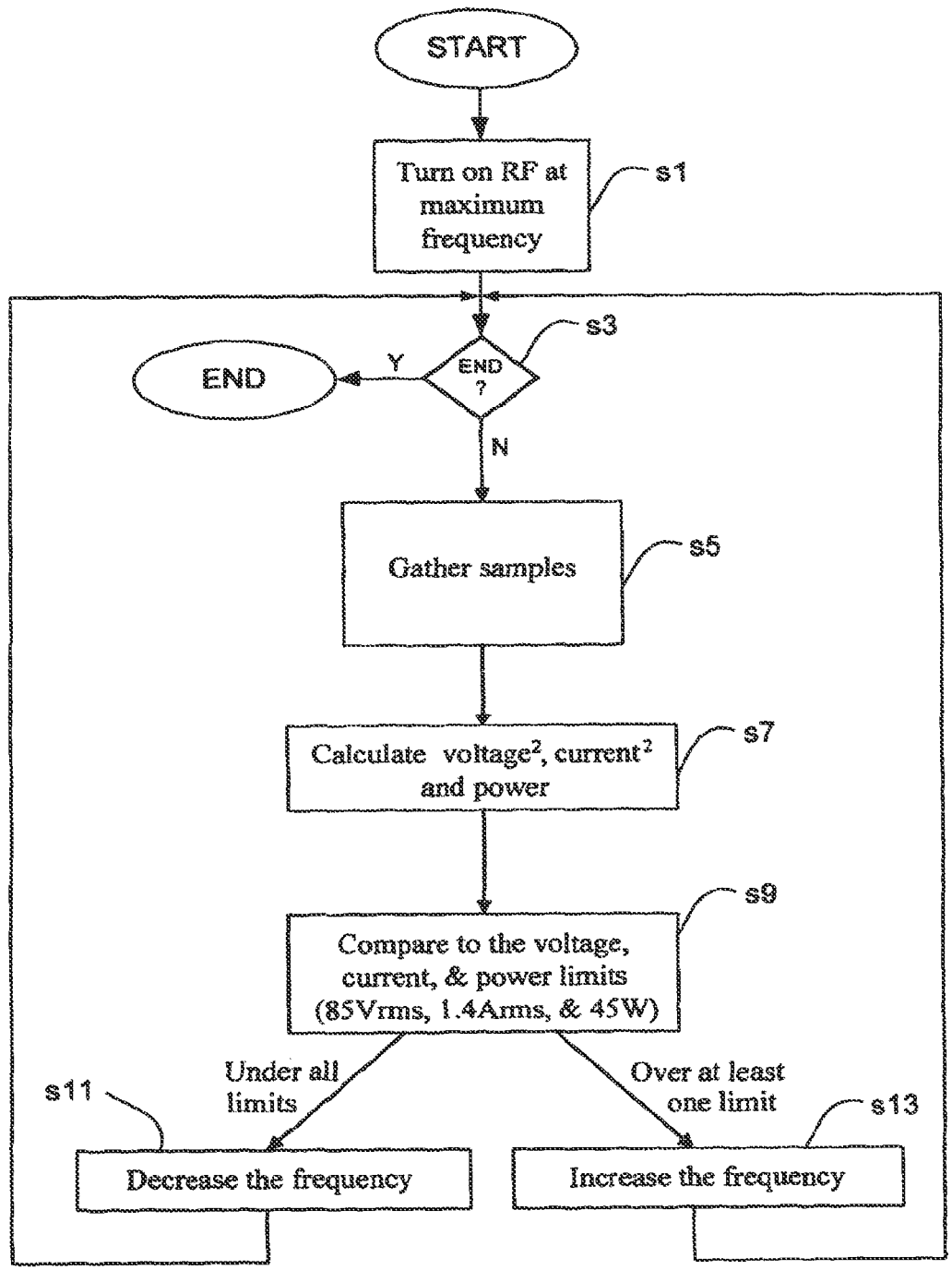
FIG. 7 is a flow chart illustrating the operation of a frequency control algorithm used to control the frequency of the RF drive signals applied to the cauterization device.

FIG. 7 illustrates the processing performed in this embodiment by the calculation module 53 and the frequency control module 55. As shown, at the beginning of the process in step s1, the control module 55 turns on the RF drive signal at the system defined maximum frequency by passing an initialisation signal to the square wave generation module 63. Provided the control module 55 has not received, in step s3, a power down signal from the medical device control module 57, the processing proceeds to step s5 where the calculation module 53 obtains the voltage and current samples from the synchronous sampling circuitry 51. In step s7 the calculation module 53 calculates the square of the voltage and the square of the current and the delivered power by multiplying the measured voltage by the measured current. These calculated values are then passed to the frequency control module 55 which compares, in step s9, the values with the defined limits for the applied voltage, current and power. The voltage and current limits are static limits that are defined in advance. However, the power limit depends on the medical procedure and is defined by the power set point ($P_{set}$) provided by the medical device control module 57. If each of the measured values is below the corresponding limit then, in step s11, the frequency control module 55 decides to decrease the drive frequency and a decrease command is passed to the square wave generator

63. At the start of the processing, the drive frequency is set to a defined maximum value (in this embodiment 500 kHz), which will always be above the resonant peak of the characteristic 65, regardless of the load impedance. Therefore, regardless of the load 39, the initial operating frequency should be on the right hand side of the resonant plot shown in FIG. 6. By decreasing the drive frequency, the drive frequency will get closer to the resonant frequency of the resonant circuit 28. As a result, the applied current will increase and more power will be delivered to the load 39. The processing then returns to step s3 and the above process is repeated.

Therefore, the current and power applied to the load 39 should increase until one of the limits is reached. At this point, the control module 55 will determine, in step s9, that a limit has been reached and so will proceed to step s13, where the control module 55 decides to increase the drive frequency and sends the square wave generation module 63 an increase command. This will cause the drive frequency to move away from the resonant frequency of the circuit 28 and so the current and power delivered to the load 39 will reduce. The processing will then return to step s3 as before.

Thus, by starting on one side of the resonant peak and slowly moving the drive frequency towards and away from the resonant peak, the current and power level applied to the load 39 can be controlled within the defined limits even as the impedance of the load changes and the resonant characteristic 65 of the resonant circuit 28 changes as the tissue/vessel is cauterised.

As those skilled in the art will appreciate, it would also be possible to start on the left hand side of the resonant peak and increase the drive frequency to increase the delivered power and decrease the drive frequency to decrease the delivered power.

Medical Device Control Module

Figure 8:
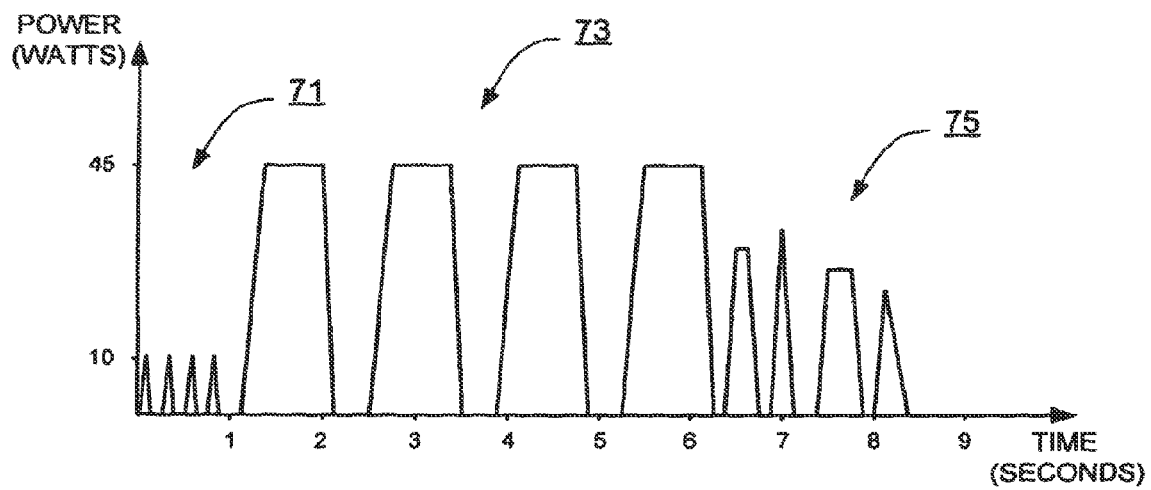
FIG. 8 is a plot illustrating one way in which the power limit can be varied by the control electronics during a surgical procedure.

As mentioned above, the medical device control module 57 controls the general operation of the cauterisation device 1. It receives user inputs via the user input module 59. These inputs may specify that the jaws of the forceps 9 are now gripping a vessel or tissue and that the user wishes to begin cauterisation. In response, in this embodiment, the medical device control module 57 initiates a cauterisation control procedure. Initially, the medical device control module 57 sends an initiation signal to the frequency control module 55 and obtains current and power measurements from the calculation module 53. The medical device control module 57 then checks the obtained values to make sure that the load 39 is not open circuit or short circuit. If it is not, then the medical device control module 57 starts to vary the power set point to perform the desired cauterisation. FIG. 8 is a plot illustrating the way in which the medical device control module 57 may vary the set point power to achieve the desired cauterisation procedure. Various other techniques and other power delivery algorithms may also be used.

As shown in FIG. 8, during an initial period 71 the medical device control module 57 pulses the set point power between zero and about 10 Watts. Then during a main cauterisation period 73 (which typically lasts for about 5 seconds) the medical device control module 57 pulses the set point power between zero and 50 Watts. During this period, the medical control device receives the power and voltage measurements from the calculation module 53 and calculates from them the impedance of the load 39. The medical device control module 57 determines that the cauterisation is complete when the calculated impedance exceeds a threshold. Finally, the medical device control module 57 performs a terminating procedure during a terminating period 75.

During the terminating procedure, the medical device control module 57 varies the set point power and checks that cauterisation has been achieved (by checking the impedance of the load using the measured power and current values) and re-enters the main cauterisation period again if it determines that cauterisation has not been completed.

Resonant Circuit Design

The way that the values of the inductors and capacitors were chosen in this embodiment will now be described. As those skilled in the art will appreciate, other design methodologies may be used.

The complex impedance of the circuit shown in FIG. 2 can be approximated by the following equation:

$$Z = j2\pi f L_s + \frac{1}{j2\pi f C_s} + \frac{j2\pi f L_m R_{load\_ref}}{j2\pi f L_m + R_{load\_ref}} + R_s \qquad (1)$$

Where:

$R_{load\_ref}$ is the load resistance referred to the primary (by the square of the turns ratio); $R_s$ represents the equivalent series resistance of the inductor, transformer capacitor and switching devices.

All other component non-idealities are ignored and the transformer is considered to be ideal as a first approximation.

Assuming that $R_s$ is small, when the load is open circuit (ie $R_{load\_ref}$ is infinite) the resonant frequency can be shown to be:

$$f_{min} = \frac{1}{2\pi\sqrt{(L_s + L_m)C_s}} \qquad (2)$$

Similarly, when the load is short circuit (ie $R_{load\_ref}$ is zero) the resonant frequency can be shown to be:

$$f_{max} = \frac{1}{2\pi\sqrt{L_s C_s}} \qquad (3)$$

Assuming $R_s$ is small, at each frequency between $f_{min}$ and $f_{max}$ there is a value of the load, $R_{load}$, at which the greatest power can be dissipated in the load. This maximum power can be shown to be large at frequencies near $f_{min}$ and $f_{max}$, and has a minimum at the critical frequency, fc. We refer to this power as $P_{max\_fc}$. Starting with (1) it can be shown that the following relationship holds:

$$L_m = \frac{2V_s^2}{2\pi f_c P_{max\_fc}} \qquad (4)$$

where $V_s$ is the supply voltage.

It can be shown that the load at which equation (4) holds is given by:

$$R_{load\_ref} = 2\pi f L_m \qquad (5)$$

Furthermore from (1) a relationship between $f_{min}$, $f_c$ and $f_{max}$ can be established:

$$f_{min} = \sqrt{(2\pi f_c)^2 \frac{(2\pi f_{max})^2 + (2\pi f_c)^2}{3(2\pi f_{max})^2 - (2\pi f_c)^2}} \qquad (6)$$

From (6) it can be shown that $f_{min} < f_c < f_{max}$. If the circuit is to operate at $f_c$, then equation (4) gives an upper bound non the worst-case power delivered across a range of loads.

From (1), it can be shown that the efficiency of the circuit at resonance may be written as:

$$\eta = \frac{\left(\frac{(2\pi f_c)^2 L_m^2 R_{load}}{(2\pi f_c)^2 L_m^2 + R_{load}^2}\right)}{Re(Z)} \quad (7)$$

$$= \frac{(2\pi f_c)^2 L_m^2 R_{load\_ref}}{R_s((2\pi f_c)^2 L_m^2 + R_{load\_ref}^2) + (2\pi f_c)^2 L_m^2 R_{load\_ref}}$$

From (7) it may be shown that the efficiency is a maximum when $R_{load\_ref} = 2\pi f L_m$, i.e. when (5) holds. Therefore the system is designed to operate around the point of maximum efficiency.

Design Procedure

For this specific embodiment of the design the following parameters were chosen:

Battery voltage of 24V however battery voltage droops with discharge and load so $V_{s\_sq} = 18V$ (square wave peak to peak voltage) when used
$P_{load} = 45$ W (maximum power into the load)
$V_{load} = 85$ Vrms (maximum voltage into the load)
$I_{load} = 1.4$ Arms (maximum current into the load)
$f_c = 430$ kHz (centre or critical switching frequency)
$f_{max} = 500$ kHz (maximum switching frequency, which is the upper resonant frequency)
$f_{min} = 380$ kHz (approximate minimum switching frequency—needs to be calculated)

Given these values, $f_{min}$ can be computed using (6):

$$f_{min} = \sqrt{(2\pi 430k)^2 \frac{(2\pi 500k)^2 + (2\pi 430k)^2}{3(2\pi 500k)^2 - (2\pi 430k)^2}}$$

$$f_{min} = 377 \text{ kHz}$$

Resonant circuits produce sinusoidal waveforms therefore the input square wave voltage ($V_{s\_sq}$) needs to be converted into the RMS of the fundamental switching frequency ($V_s$).

$$V_s = \frac{4}{\pi} \frac{V_{s\_sq}}{2\sqrt{2}}$$

$$= \frac{4}{\pi} \frac{18 \text{ V}}{2\sqrt{2}}$$

$$= 8.1 V_{rms}$$

The power into the load ($P_{load}$) is set by $L_m$. Using (4) the transformer magnetising inductance (Lm) can be determined. This ensures that at the critical frequency, $f_c$, the required power is delivered:

$$L_m = \frac{2V_s^2}{2\pi f_c P_{load}}$$

$$= \frac{2 \times 8.1 V_{rms}^2}{2\pi \times 430 \text{ kHz} \times 45 \text{ W}}$$

$$= 1.08 \text{ }\mu\text{H}$$

$L_s$ can then be calculated (derived from equations 2 & 3):

$$L_s = \frac{L_m}{\frac{f_{max}^2}{f_{min}^2} - 1}$$

$$= \frac{1.08 \text{ }\mu\text{H}}{\frac{500 \text{ kHz}}{377 \text{ kHz}} - 1}$$

$$= 1.43 \text{ }\mu\text{H}$$

Following from this $C_s$ can be calculated (from equation 3):

$$C_s = \frac{1}{L_s(2\pi f_{max})^2}$$

$$= \frac{1}{1.43 \text{ }\mu\text{H}(2\pi 500 \text{ kHz})^2}$$

$$= 71 \text{ nF}$$

To maintain regulation, the circuit is run above resonance so actual values of $C_s$ will be typically 20% higher to bring the operating point back down (if below resonance was chosen $C_s$ would have to be reduced).

As previously mentioned, the efficiency is maximized when $R_{load\_ref}$ is equal to the magnetising reactance at the critical frequency (equation 5). It is desirable, therefore, to operate about the middle of the constant power range (shown in FIG. 5b). $R_{load\_upper}$ is the load resistance at which constant power changes to constant voltage. Similarly, $R_{load\_lower}$ is the load resistance at which constant power changes to constant current.

$$R_{load\_upper} = \frac{V_{load}^2}{P}$$

$$= \frac{85 V_{rms}^2}{45 \text{ W}}$$

$$= 161 \text{ }\Omega$$

$$R_{load\_lower} = \frac{P}{I_{load}^2}$$

$$= \frac{45 \text{ W}}{1.4 A^2}$$

$$= 23 \text{ }\Omega$$

Take the geometric mean of these load resistances to find $R_{load\_c}$ (centre or critical load resistance)

$$R_{load\_c} = \sqrt{R_{load\_upper} R_{load\_lower}}$$

$$= 60 \text{ }\Omega$$

As discussed, for maximum efficiency, $R_{load\_ref}$ should match the impedance of the primary-referred magnetising reactance at fc. Hence, $R_{load}$ should equal the secondary-referred magnetising reactance $L_{sec}$ can therefore be calculated as follows:

$$L_{sec} = \frac{R_{load\_c}}{2\pi f_c}$$

$$= \frac{60}{2\pi 430 \text{ kHz}}$$

$$= 22.2 \text{ μH}$$

Finally the transformer turns ratio can be calculated:

$$N = \sqrt{\frac{L_{sec}}{L_m}}$$

$$= \sqrt{\frac{22.2 \text{ μH}}{1.08 \text{ μH}}}$$

$$= 4.5$$

For any particular design it may be necessary to adjust the values due to the following reasons:
to maximise efficiency
compensate non ideal effect of components (e.g. series resistance, parasitic capacitance & inductance, non ideal transformer characteristics such as leakage inductance)
make the design practical (e.g. use standard values of capacitors and a whole number of turns
allow margin to meet the requirements due to component tolerances, temperature etc.

In this specific embodiment, the component values were optimized to:
Cs=82 nf
Lm=1.1 uH
Ls=1.4 uH
N=5 which gives Lsec≈24 uH The following subsections briefly describe how these component values were physically implemented.

Capacitor Selection

A low loss capacitor is desired to minimise tosses and to ensure the component doesn't get too hot. Ceramic capacitors are ideal and the dielectric type of COG/NPO were used in this embodiment. The capacitor voltage rating is also important as it shouldn't be exceeded under all load conditions. Ten 250V 8.2 nF 1206 COG/NPO ceramics capacitors in parallel were used in this embodiment.

Inductor and Transformer

In this embodiment, Ferroxcube 3F3 E3216/20 a-core/plate combination was used as a ferrite core. Ferroxcube 3F3 is supplied by Ferroxcube, a subsidiary of Yageo Corporation, Taiwan. It is a high frequency ferrite material optimised for frequencies between 200 kHz and 500 kHz. By using this material the core losses are minimised. Core losses increase strongly with increasing flux density. In an inductor, for a particular required energy storage, the flux density increases with decreasing air gap (the air gap is the separation between the e-core & plate). Therefore the air gap and the number of turns can be increased to decrease core losses but this has to be balanced with the actual inductance value required and increased resistive losses introduced with the longer wire/track length.

The same issues apply to the transformer except core losses are due to the output voltage and the number of turns. Since the output voltage is fixed the number of turns is the only variable that can be changed but again this has to be balanced with resistive losses. Once the number of turns is set the air gap can then be adjusted to set Lm. Whatever core is used, it is best practise to fill the winding space with as much copper as possible to minimise resistive losses. In the transformer the' volume of windings is preferably about the same in the primary and secondary to balance the losses.

The resistive losses can usually be easily calculated but since the circuit is operating at about 400 kHz skin depth becomes an issue. The skin depth in copper at 400 kHz is only about 0.1 mm so a solid conductor thicker than this doesn't result in all the copper being used. Litz wire (stranded insulated copper wire twisted together where each strand is thinner than the skin depth) can be used to reduce this effect. In this embodiment 2 oz PCB tracks (about 0.07 mm thick copper tracks) were used for the windings of both the inductor ($L_s$) and the transformer to avoid having to wind custom components. The inductor had two turns with an air gap of 0.5 mm between the e-core and plate. The transformer had one turn on the primary and five turns on the secondary with an air gap between the e-core and plate of 0.1 mm.

Modifications and Alternatives

A medical cauterisation device has been described above. As those skilled in the art will appreciate, various modifications can be made and some of these will now be described. Other modifications will be apparent to those skilled in the art.

In the above embodiment, various operating frequencies, currents, voltages etc were described. As those skilled in the art will appreciate, the exact currents, voltages, frequencies, capacitor values, inductor values etc. can all be varied depending on the application and the values described above should not be considered as limiting in any way. However, in general terms, the circuit described above has been designed to provide an RF drive signal to a medical device, where the delivered power is desired to be at least 10 W and preferably between 10 W and 200 W; the delivered voltage is desired to be at least 20 $V_{rms}$ and preferably between 30 $V_{rms}$ and 120 $V_{rms}$; the delivered current is designed to be at least 0.5 $A_{rms}$ and preferably between 1 $A_{rms}$ and 2 $A_{rms}$; and the drive frequency is at least 50 kHz.

Figure 9:
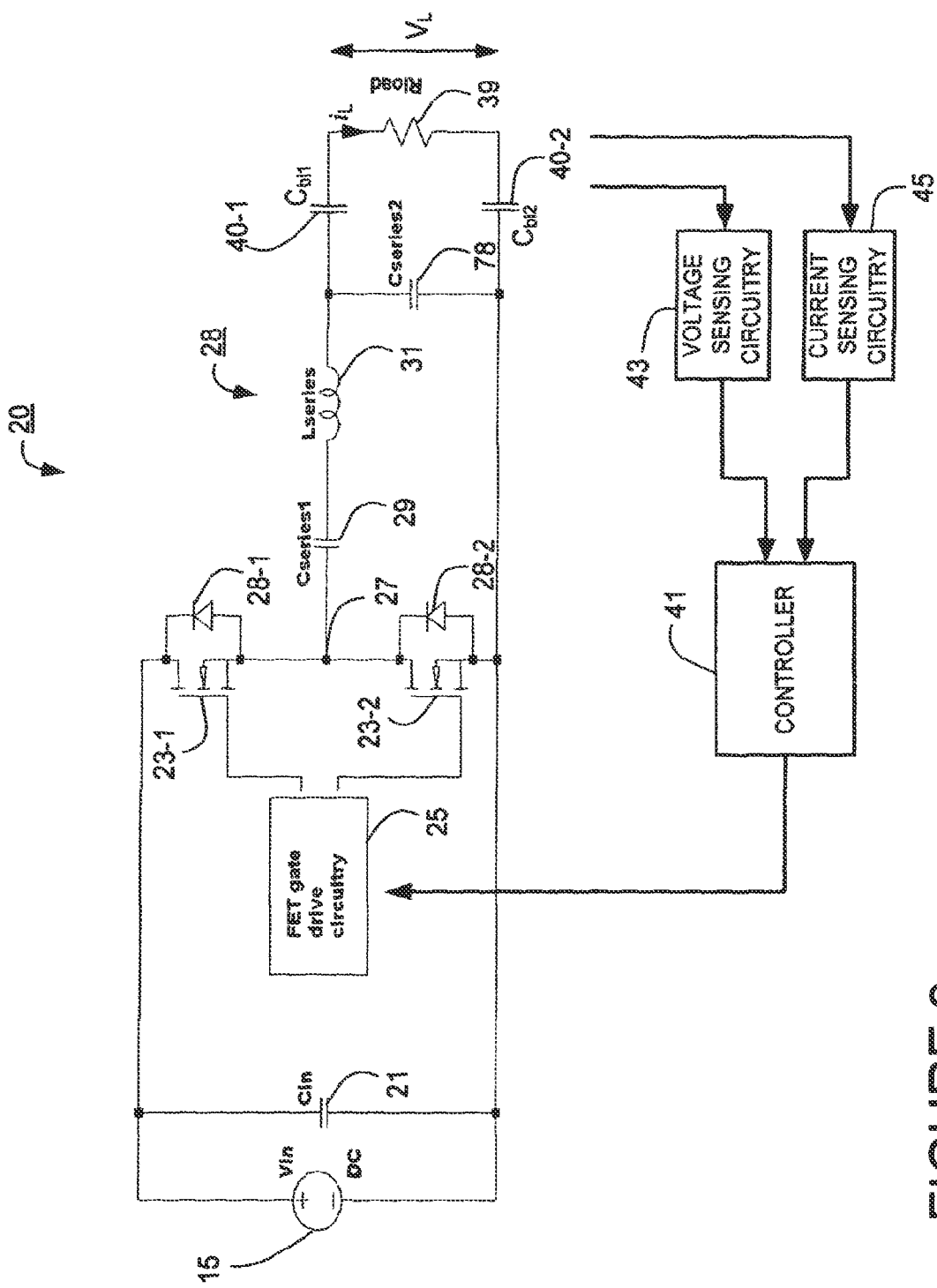
FIG. 9 is a part block part schematic diagram illustrating the main components of another RF drive circuit and control circuit embodying the invention.
Figure 10:
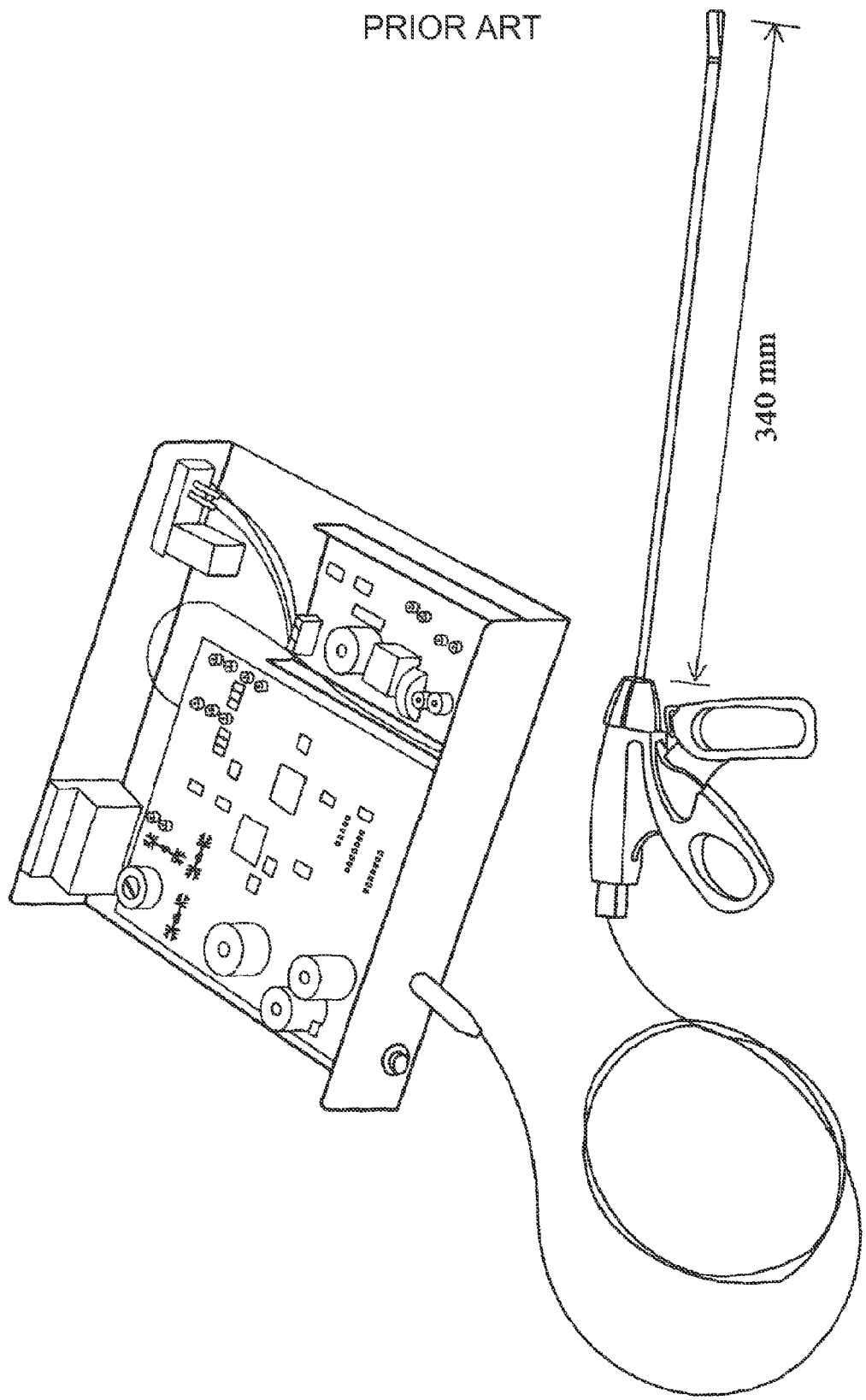
FIG. 10 illustrates the form of a prior art hand-held cauterization device which is connected to power supply and control electronics via a power supply line.
Figure 11:
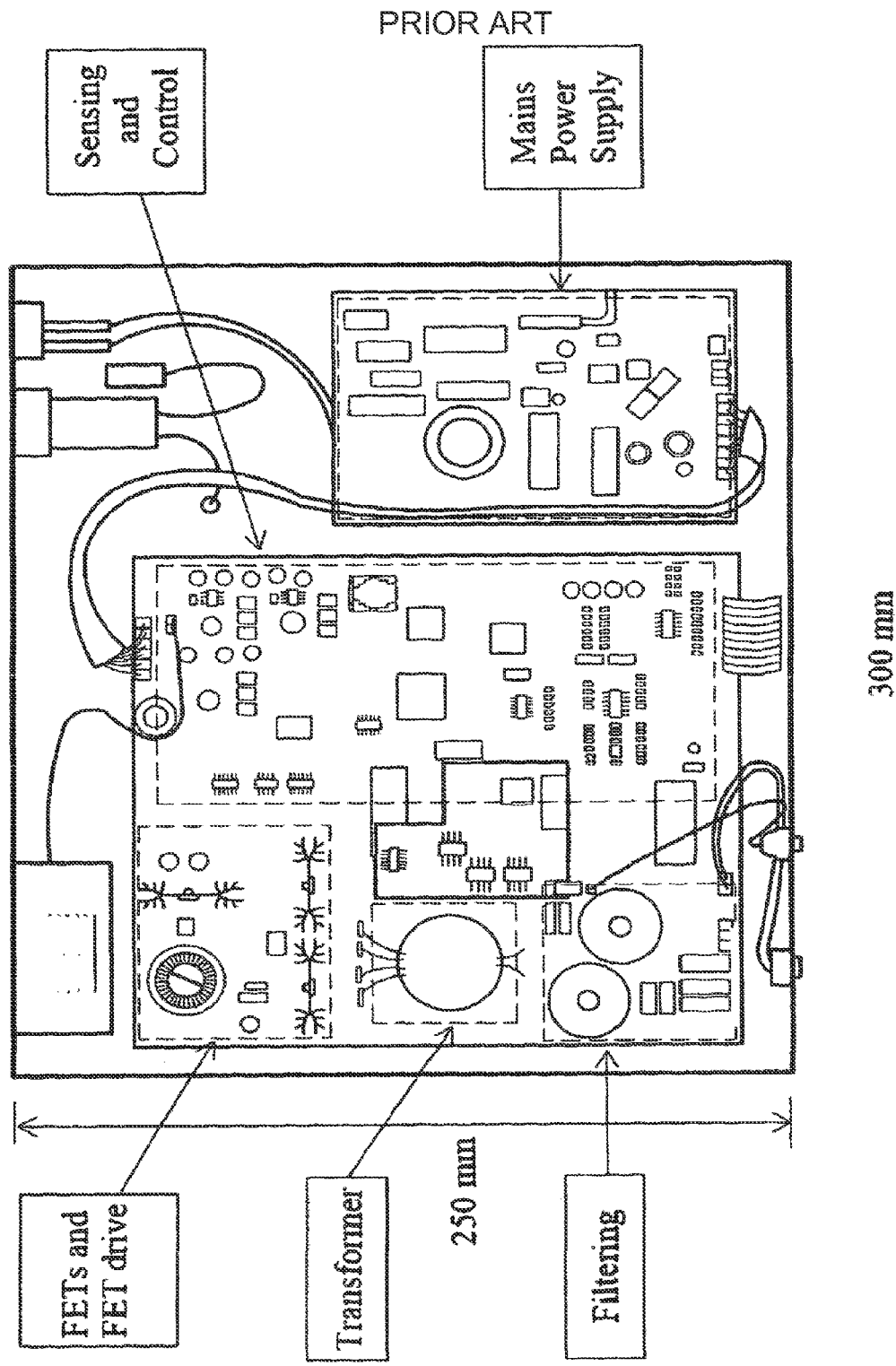
FIG. 11 is a plan view illustrating the different components of the existing electronics used to drive and control the hand-held cauterization device illustrated in FIG. 10.

In the above embodiment, the resonant circuit 28 was formed from capacitor-inductor-inductor elements. As those skilled in the art will appreciate, the resonant circuit 28 can be formed from various circuit designs. FIG. 9 illustrates another resonant circuit design that can be used in other embodiments. In the design shown in FIG. 9, the resonant circuit 28 is formed from capacitor-inductor-capacitor elements, with the load being connected across the second capacitor 78. As shown, in this design, there is no transformer and so there is no step-up in voltage. However, the operation of this embodiment would still be the same as in the embodiment described above and so a further description shall be omitted. Other resonant circuit designs with multiple capacitors and inductors in various series and parallel configurations or simpler LC resonant circuits may also be used.

FIG. 1 illustrates one way in which the batteries and the control electronics can be mounted within the handle of the medical device. As those skilled in the art will appreciate, the form factor of the handle may take many different designs.

In the above embodiment, an exemplary control algorithm for performing the cauterisation of the vessel or tissue gripped by the forceps was described. As those skilled in the art will appreciate, various different procedures may be used and the reader is referred to the literature describing the operation of cauterisation devices for further details In the above embodiment, the RF drive signal generated by the drive circuitry was directly applied to the two forceps jaws of the medical device. In an alternative embodiment, the drive signal may be applied to one jaw, with the return or ground plane being provided through a separate connection on the tissue or vessel to be cauterised.

In the above embodiments, the forceps jaws were used as the electrodes of the medical device. In an alternative device, the electrodes may be provided separately from the jaws.

In the above embodiments, two FET switches were used to convert the DC voltage provided by the batteries into an alternating signal at the desired RF frequency. As those skilled in the art will appreciate, it is not necessary to use two switches—one switch may be used instead or multiple switches may be used connected, for example, in a bridge configuration. Additionally, although FET switches were used, other switching devices, such as bipolar switches may be used instead. However, MOSFETs are preferred due to their superior performance in terms of low losses when operating at the above described frequencies and current levels.

In the above embodiment, the resonant circuit 28 acted as a frequency dependent attenuator. The resonant circuit was designed as a substantially lossless attenuator, but this is not essential The resonant circuit may include lossy components as well, although the resulting circuit will of course be less efficient.

In the above embodiment, the I & Q sampling circuitry 51 sampled the sensed voltage/current signal once every period and combined samples from adjacent periods. As those skilled in the art will appreciate, this is not essential. Because of the synchronous nature of the sampling, samples may be taken more than once per period or once every nth period if desired. The sampling rate used in the above embodiment was chosen to maximise the rate at which measurements were made available to the medical device control module 57 as this allows for better control of the applied power during the cauterisation process.

In the above embodiment, a 24V DC supply was provided. In other embodiments, lower DC voltage sources may be provided. In this case, a larger transformer turns ratio may be provided to increase the load voltage to a desired level or lower operating voltages may be used.

In the above embodiment, a synchronous sampling technique was used to obtain measurements of the load voltage and load current. As those skilled in the art will appreciate, this is not essential and other more conventional sampling techniques can be used instead.

In the above embodiment, the medical device was arranged to deliver a desired power to the electrodes of the end effector. In an alternative embodiment, the device may be arranged to deliver a desired current or voltage level to the electrodes of the end effector.

In the above embodiment the battery is shown integral to the medical device. In an alternative embodiment the battery may be packaged so as to clip on a bell on the surgeon or simply be placed on the Mayo stand. In this embodiment a relatively small two conductor cable would connect the battery pack to the medical device.

The invention claimed is:

1. A medical device comprising:
a handle for gripping by a user, an end effector coupled to the handle and having at least one electrical contact;
a radio frequency (RF) generation circuit coupled to the handle and operable to generate an RF drive signal and to provide the RF drive signal to the at least one electrical contact, wherein the RF generation circuit comprises a resonant circuit; and
a control circuit comprising a sampling circuit, wherein the control circuit is configured to vary a frequency of the RF drive signal around a resonant frequency of the resonant circuit and configured to determine the frequency and a phase of the RF drive signal and generate a sampling frequency, and wherein the sampling circuit is configured to sample a sensed voltage signal or a sensed current signal at the sampling frequency, such that the sampling frequency is synchronized with the frequency and the phase of the RF drive signal.

2. The device according to claim 1, wherein the RF generation circuit comprises switching circuitry configured to generate a cyclically varying signal from a DC supply and wherein the resonant circuit is configured to receive the cyclically varying signal.

3. The device according to claim 2, wherein the cyclically varying signal is a square wave signal.

4. The device according to claim 1 comprising a battery compartment for holding one or more batteries for providing power to the RF generation circuit for generating the RF drive signal.

5. The device according to claim 4, wherein the battery compartment is configured to hold a module comprising the one or more batteries and the RF generation circuit.

6. The device according to claim 1, further comprising:
battery terminals for connecting to one or more batteries;
wherein the RF generation circuit is coupled to the battery terminals;
wherein the RF generation circuit further comprises:
switching circuitry for generating a cyclically varying signal from a potential difference across the battery terminals; and
the resonant circuit, being a resonant drive circuit coupled to the switching circuitry and operable to filter the cyclically varying signal generated by the switching circuitry; and wherein the RF drive signal is controlled by an output from the resonant drive circuit.

7. The device according to claim 1, wherein the control circuit is operable to receive a measurement of the RF drive signal and is operable to vary the frequency of the RF drive signal to control a power, a voltage or a current delivered to the at least one electrical contact of the end effector.

8. The device according to claim 7, wherein the measurement is obtained from the sampling circuit.

9. The device according to claim 1, wherein the control circuit is further configured to generate the sampling frequency as an integer fraction of the frequency of the RF drive signal.

10. The device according to claim 1, wherein the resonant circuit has a resonant characteristic, the resonant characteristic varying with a load connected to the at least one electrical contact, and wherein the control circuit is configured to vary the frequency of the RF drive signal to track changes in the resonant characteristic of the resonant circuit.

11. A medical device comprising:
a handle for gripping by a user;
an end effector coupled to the handle and having at least one electrical contact;
a radio frequency (RF) generation circuit operable to generate an RF drive signal and to provide the RF drive signal to the at least one electrical contact;
a frequency dependent attenuator comprising a resonant circuit; and
a control circuit comprising a sampling circuit, wherein the control circuit is operable to vary a frequency of the RF drive signal around a resonant frequency of the resonant circuit to control at least one of a power, a voltage or a current provided to the at least one contact of the end effector and is configured to determine the frequency and a phase of the RF drive signal and generate a sampling frequency, and wherein the sampling circuit is configured to sample a sensed voltage signal or a sensed current signal at the sampling frequency, such that the sampling frequency is synchronized with the frequency and the phase of the RF drive signal.

12. The device according to claim 11, wherein the RF generation circuit comprises a signal generator operable to generate a cyclically varying signal at a frequency; and the frequency dependent attenuator is configured to attenuate the cyclically varying signal in dependence upon the frequency of the cyclically varying signal.

13. The device according to claim 12, wherein the resonant frequency is at or near the frequency of the cyclically varying signal.

14. The device according to claim 11, further comprising:
- an input for receiving a sensed signal that varies with the RF drive signal applied to the at least one electrical contact; and
- a measurement circuit operable to make measurements of the RF drive signal using samples obtained from the sampling circuit;
- wherein the control circuit is operable to control the RF generation circuit in dependence upon the measurements made by the measurement circuit, to vary the frequency of the RF drive signal.

* * * * *